US010828258B2

(12) United States Patent
Ognibene et al.

(10) Patent No.: US 10,828,258 B2
(45) Date of Patent: Nov. 10, 2020

(54) DIRECTLY COMPRESSIBLE COMPOSITION COMPRISING MICROCRYSTALLINE CELLULOSE

(71) Applicant: Merck Patent GmbH, Darmstadt (DE)

(72) Inventors: Roberto Ognibene, Darmstadt (DE); Finn Bauer, Bensheim (DE); Thorsten Wedel, Stockstadt/Rhein (DE); Guenter Moddelmog, Reinheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/032,721

(22) Filed: Jul. 11, 2018

(65) Prior Publication Data
US 2018/0318224 A1 Nov. 8, 2018

Related U.S. Application Data

(62) Division of application No. 15/329,620, filed as application No. PCT/EP2015/001356 on Jul. 3, 2015, now abandoned.

(30) Foreign Application Priority Data

Jul. 30, 2014 (EP) .................................. 14002665

(51) Int. Cl.
*A61K 9/20* (2006.01)
(52) U.S. Cl.
CPC .......... *A61K 9/2054* (2013.01); *A61K 9/2027* (2013.01)
(58) Field of Classification Search
CPC ............................. A61K 9/2027; A61K 9/2054
See application file for complete search history.

(56) References Cited

U.S. PATENT DOCUMENTS

| 4,990,335 | A | 2/1991 | Bateman | |
|---|---|---|---|---|
| 10,028,915 | B2 | 7/2018 | Furo et al. | |
| 2005/0220881 | A1* | 10/2005 | Mehta | A61K 9/1641 424/486 |
| 2005/0250838 | A1* | 11/2005 | Challapalli | A61K 9/2031 514/419 |
| 2006/0039967 | A1* | 2/2006 | Ohta | A61K 9/0056 424/464 |
| 2007/0020335 | A1* | 1/2007 | Chen | A61K 9/205 424/486 |

(Continued)

FOREIGN PATENT DOCUMENTS

| EP | 2578208 A1 * | 4/2013 | ............ A61K 31/40 |
| JP | 02502720 A | 8/1990 | |

(Continued)

OTHER PUBLICATIONS

Mowiol, "Technical data sheet", Jun. 2010, (Year: 2010).*

(Continued)

*Primary Examiner* — Jianfeng Song
(74) *Attorney, Agent, or Firm* — Millen White Zelano and Branigan, PC; Csaba Henter

(57) ABSTRACT

The present invention relates to a directly compressible composition for the production of tablets which comprise fine-grained polyvinyl alcohols (PVAs) and fine-grained microcrystalline celluloses (MCCs) in a co-mixture. The present invention also relates to the use of this mixture and to a process for the preparation thereof.

13 Claims, 4 Drawing Sheets

(56) References Cited

U.S. PATENT DOCUMENTS

| | | | |
|---|---|---|---|
| 2008/0020055 A1* | 1/2008 | Monteith | A61K 9/2054 424/497 |
| 2008/0138404 A1* | 6/2008 | Walsh | A61K 9/2031 424/452 |
| 2008/0152595 A1* | 6/2008 | Emigh | A61K 9/0043 424/10.4 |
| 2008/0305165 A1 | 12/2008 | Noh et al. | |
| 2011/0064830 A1* | 3/2011 | Muller | A61K 9/0056 424/724 |
| 2011/0129530 A1* | 6/2011 | Venkatesh | A61K 9/0056 424/470 |
| 2013/0287847 A1* | 10/2013 | Bodmeier | A61K 9/146 424/464 |
| 2014/0221426 A1* | 8/2014 | Gerk | A61K 45/06 514/321 |
| 2016/0143851 A1 | 5/2016 | Karavas et al. | |

FOREIGN PATENT DOCUMENTS

| | | |
|---|---|---|
| JP | 2011148832 A | 7/2013 |
| WO | 88/07366 A1 | 10/1988 |
| WO | 2011037976 A2 | 3/2011 |
| WO | 2016/013675 A | 1/2016 |

OTHER PUBLICATIONS

Sigma-Aldrich, "Mowiol 18-88", retrieved from https://www.signnaaldrich.conn/catalog/product/aldrich/81365?lang=en&region=US on Mar. 22, 2018. (Year: 2018).*
International Search Report dated Aug. 10, 2015 issued in corresponding PCT/EP2015/001356 application (2 pages).
MilliporeSigma, "Our Emprove quality PVA", Jun. 20, 2013. (Year: 2013).
Sigma Aldrich, "Polyvinyl alcohol 18-88", retrieved from https://www.sigmaaldrich.com/catalog/product/mm/141355?lang=en&region=US on Mar. 22, 2018. (Year:2018).
MerkMillipore, "A list of advantages for the globe market", Mar. 2013. (Year: 2013).
Notification of Reasons for Refusal dated Mar. 4, 2019 in corresponding Japan (JP 2017-505122) pp. 1-5 (and english translation pp. 1-4).
Du Pont: "Avicel for Solid Dose Form", downloaded from JPO on Oct. 3, 2018, author unknown, 1 page.
Catalog of Ceolus, downloaded from JPO on Oct. 3, 2018, author unknown, 1 page.
USP monographs, 2015 Official May 1, 2016-Jul. 31, 2016 Polyvinyl Alcohol ,author unknown, (pp. 1-4).
Eur. Pharmacopoeia 8.7:, Polyvinyl Alcohol ,downloaded from JPO on Oct. 3, 2018, author unknown, (pp. 5800-5801).
Notice of Submission in corresponding JP20172-505122 dated Sep. 12, 2018 (1 page).

* cited by examiner

DIRECTLY COMPRESSIBLE COMPOSITION COMPRISING MICROCRYSTALLINE CELLULOSE

The present invention relates to a directly compressible composition for the production of tablets which comprise fine-grained polyvinyl alcohols (PVAs) and fine-grained microcrystalline celluloses (MCCs) in a co-mixture. The present invention also relates to the use of this mixture and to a process for the preparation thereof.

PRIOR ART

Polyvinyl alcohols (PVAs) are synthetic polymers which are available in various grades, in particular with respect to degree of polymerisation and their viscosity. Polyvinyl alcohols are obtained by alkaline hydrolysis of polyvinyl acetate. Polyvinyl acetate is in turn obtained by free-radical polymerisation from vinyl acetate. Through different chain lengths and different degrees of hydrolysis of the polyvinyl acetates employed, polyvinyl alcohols (PVAs) having a very wide variety of physical properties can be obtained. Polyvinyl alcohols are employed, in particular, as film formers, adhesive gels and as viscosity modulator, in a multiplicity of areas of application, for example paints, papers, textiles, cosmetics and in pharmaceuticals, including drug delivery systems, etc.

In the pharmaceutical industry, the use of PVAs is particularly interesting in pharmaceutical preparations, such as, for example, in ophthalmic preparations, as film formers for coated tablets, as binders in granules or as coating component in plasters, and also in drug delivery systems. Of very particular interest is the use of various PVA grades in the formulation of solid oral pharmaceutical administration forms having extended release of active compound, for example in so-called "retard tablets". In these tablets, the active compound is in finely divided form in a PVA matrix.

After taking orally, delayed release of active compound from polymer-containing pharmaceutical formulations of this type is achieved through the tablets not dissolving directly in the presence of liquid, such as in the mouth or gastrointestinal tract, but instead swelling and a gel forms from which the active compound is only released little by little by diffusion and slow erosion of the gel matrix in the gastrointestinal tract. This delayed release of active compound from the retard tablets in turn results in an approximately constant level of active compound in the blood and thus in an improved therapeutic effect.

This means that galenically modified tablets of this type enable the active compound to be released from the administration form in a controlled manner over an extended time in the body, in order thus to maintain a therapeutically effective blood level of the medicament over an extended period (several hours).

The two essential advantages of such retarded formulations are—in contrast to tablets having immediate release of active compound after taking—firstly the avoidance of undesired, possibly also toxic blood/plasma levels of the API (API: active pharmaceutical ingredient) and also a reduction in the frequency with which the tablets are taken (for example only once/daily instead of three times/daily) and thus an improvement in so-called patient compliance, which is in turn associated with an improved therapeutic outcome of the medicinal treatment.

Known polyvinyl alcohols which are specified for use in pharmaceutical formulations according to the various pharmacopoeias (Pharmacopoea Europaea, Ph. Eur.; United States Pharmacopoeia (USP), and the Japanese Pharmacopoeia (JP or JPE), but cannot be tableted directly by the action of pressure or only under particular conditions.

A particular problem in this connection thus consists in the production in a simple manner of tablets which principally consist of corresponding PVAs as active compound excipient in which the active compound is homogeneously distributed. Direct tabletability of PVA-containing formulations can usually only be achieved in the presence of relatively high proportions of further binders, such as lactose, and of lubricants and possibly further additives. Formulations in which PVAs are employed as active compound excipient are frequently prepared in the presence of aqueous or alcoholic solutions. For example, it is known to produce corresponding tablets having extended release of active compound by compressing the active compound and PVA in the presence of further additives after wet granulation. The latter is associated with the disadvantage that the solvents necessary for wet granulation have to be removed again with high input of energy.

OBJECT OF THE PRESENT INVENTION

As can be seen from the description above, swelling polymers, from which the active compound is released in a time-controlled manner via diffusion and erosion processes after moistening, for example, in the stomach and intestine and made available for resorption, are frequently employed in order to achieve the desired retardation effects.

Polyvinyl alcohols (PVAs) are usually used if, for example, incompatibility reactions exist between active compound and the hydroxypropylmethylcelluloses (HPMCs) frequently used as retardation polymer or if the HPMC grades employed exhibit an unsatisfactory release profile of the active compound.

For rapid tablet development with retardation effect, the pharmaceutical formulation scientist requires a swelling polymer which is directly compressible and nevertheless releases the active compound in a time-controlled manner. However, known pulverulent PVAs are per se not directly compressible and give tablets of unsatisfactory hardness which cannot be handled in pharmaceutical practice, since, for example, they have an undesired tendency to break or have excessively high abrasion.

For rapid development of such retard tablets based on polyvinyl alcohols, directly compressible polyvinyl alcohol excipient materials are therefore desirable. Excipient materials of this type would make inconvenient and expensive granulation steps, which are usually necessary in order to make the tableting mixtures compressible, superfluous.

The object of the present invention is therefore to provide directly compressible retardation matrices which make time-consuming granulation processes superfluous; i.e. steps which consist of moistening with granulation liquids, mechanical mixing in mixing systems or in fluidised-bed equipment, and post-drying processes for the removal of the granulation liquids and sieving, so that time and energy can be saved, but also expensive and time-consuming investment in special granulation equipment. The object of the present invention is also to provide advantageous directly compressible retardation matrices of this type based on compositions consisting predominantly of PVAs. In addition, it is an object of the present invention to provide a process by means of which PVAs, or commercially available PVA grades, can be converted into a directly compressible state.

BRIEF DESCRIPTION OF THE INVENTION

The present invention relates to directly compressible co-mixtures which comprise fine-grained polyvinyl alcohols (PVAs) and fine-grained microcrystalline celluloses (MCCs) and by means of which the pharmaceutical formulation scientist is provided with directly compressible compositions having retarded release of active compound. The present invention preferably relates to mixtures in which the fine-grained polyvinyl alcohols (PVAs) and fine-grained microcrystalline celluloses (MCCs) employed meet the requirements of the pharmacopoeias (Ph. Eur., USP/NF and JPE. The object of the present invention is achieved, in particular, by directly compressible co-mixtures, comprising fine-grained microcrystalline celluloses having average particle sizes of $D_{v50}$<100 μm, preferably having average particle sizes of $D_{v50}$<65 μm, particularly preferably having average particle sizes $D_{v50}$<20 μm, in particular in the range of $D_{v50}$ 1 μm-20 μm.

Directly compressible co-mixtures according to the invention having improved properties comprise the fine-grained polyvinyl alcohols and fine-grained microcrystalline celluloses described in a ratio of 5:1 to 1:5, based on the weight, preferably in a ratio in the range from 2:1 to 1:2, especially preferably in a ratio in the region of 1:1.

In accordance with the invention, corresponding directly compressible compositions may comprise fine-grained polyvinyl alcohols (PVAs) of grades 18-88, 26-88 and 40-88 which conform to the pharmacopoeias Ph. Eur., JPE and USP and all grades in between, and grade 28-99, which conforms to JPE and Ph. Eur.

The object of the present invention is achieved, in particular, by directly compressible co-mixtures, comprising fine-grained polyvinyl alcohols (PVAs) which conform to Ph. Eur. and which have been obtained by polymerisation of vinyl acetate and by subsequent partial or virtually complete hydrolysis of the polyvinyl acetate. Particularly suitable fine-grained PVAs of this type of those which have an average relative molecular weight and range between 20,000 and 150,000 g/mol, and which have a viscosity, according to Ph. Eur., In the range 3-70 mPa·s, (measured in a 4% solution at 20° C.) and have an ester value of not greater than 280 mg KOH/g (degree of hydrolysis >72.2 mol %).

Especially suitable are corresponding directly compressible co-mixtures which comprise polyvinyl alcohols (PVAs) which are water-swellable resins which, according to USP, are characterised by the formula

in which n denotes an integer in the range from 500 and up to 5,000, and which have been obtained by 85-89% hydrolysis of the polyvinyl acetate.

In addition, the present invention also relates to active compound-containing tablets having extended release of active compound over several hours, more precisely tablets comprising a co-mixture of fine-grained polyvinyl alcohols (PVAs) and fine-grained microcrystalline celluloses (MCCs), as characterised above.

In addition, it has been found that active compound-containing tablets which comprise a corresponding directly compressible co-mixture in an amount of 1-99% by weight, preferably in an amount of 5-95% by weight, very particularly preferably in an amount of 10-90% by weight, based on the total weight of the tablet, have the desired, extended release of active compound.

Tablets having particularly high tablet hardnesses which require surprisingly low ejection forces in the production process, and which have only low friabilities of ≤0.2% by weight, can advantageously be obtained with such compositions, even on use of low pressing forces.

Even on use of co-mixtures according to the invention by the action of a pressing force of 10 kN, tablets having a tablet hardness of ≥53 kN are obtained with a friability of ≤0.2% by weight. By compression with a pressing force of 20 kN, use of the co-mixtures according to the invention gives tablets having hardnesses of ≥289N which have friabilities of ≤0.1% by weight.

Tablets having delayed release of active compound which preferably comprise active compounds from BCS class I, either alone or in combination with other active compounds, can be produced particularly well using the co-mixtures described. If desired and if there is a clinical necessity, however, active compounds from other BCS classes can also be converted into directly compressible administration forms having retarded release of active compound by means of the process according to the invention.

DETAILED DESCRIPTION OF THE INVENTION

Adequate efficacy of medicaments frequently depends on uniform dosing and requires multiple administration per day so that undesired side effects can be avoided. However, this is not desirable with respect to patient compliance. For the administration of certain active compounds, it is therefore desirable to be able to provide tablet formulations by means of which release of active compound proceeds slowly over hours, so that, when taken regularly, a substantially constant effective blood level becomes established over the day, but it is only necessary to take once per day.

The demands made of the respective composition vary depending on the active compounds to be employed. Depending on their chemical and physical properties, other active compound excipients and tableting aids have to be used, since not every active compound is compatible with every tableting aid or cannot be processed with one another owing to the chemical and physical properties.

The bioavailability of active compounds can be classified in accordance with a Biopharmaceutics Classification System (BCS), which was developed by Gordon Amidon in the USA in the mid-1990s and has now become part of both a US FDA (Food And Drug Administration) guideline and also a European Medicines Agency guideline for assessment of the bioequivalence of medicaments.

For example, active compounds in BCS class I are active compounds having high solubility and high permeability. Their resorption is controlled only by the speed of stomach and intestine emptying. In the case of active compounds which belong to this class, but whose efficacy is desired over the entire day, attempts are being made to develop formulations which enable delayed, uniform release of active compound.

The Biopharmaceutics Classification System (BCS for short) describes correlations which play an important role in the oral administration of drugs. The system is based on the paper by G. Amidon and colleagues from 1995. In this paper, the authors describe that the oral bioavailability of drugs is influenced principally by their solubility, the dissolution rate and the permeability through biological membranes (Amidon G L, Lennernas H, Shah V P, Crison J R. A theoretical basis for a biopharmaceutic drug classification: the correlation of in vitro product dissolution and in vivo bioavailability. Pharm Res. 1995; 12:413.)

In the case of active compounds in BCS class 1, both the solubility and the permeability are high.

This means that, if both the solubility and also the permeability of the drug are high, it can be assumed that the absorption rate is determined principally by the rate of stomach and intestine emptying.

Since August 2000, the BCS system has been used in the approval process for proprietary medicinal products of the American approval authority for medicines, the FDA (Food And Drug Administration). Under certain prerequisites, bioavailability and bioequivalence studies can be waived in the application for approval of proprietary medicinal products if it is demonstrated using the BCS system that the new proprietary medicinal product (PMP) and a PMP which has already been approved for the same drug must be bioequivalent. An application can then be made for a waiver of the obligation to carry out these expensive and in this case unnecessary bioavailability studies. To this end, the drug in the respective medicinal form must meet certain requirements with respect to the principal parameters solubility, permeability and dissolution rate.

Solubility:

The highest dose of the drug must dissolve completely in a maximum of 250 ml of an aqueous dissolution medium in a pH range between pH 1 and pH 7.5.

Permeability:

A drug has high permeability if at least 90% of an administered dose is absorbed by the body. This must be demonstrated by suitable data (for example mass balance studies).

Dissolution Rate:

The medicinal form must ensure rapid release of the drug. This must be demonstrated by suitable in vitro release tests (either rotating basket or rotating paddle method). At least 85% of the corresponding dose must be released within 30 minutes in three different release media (0.1 N HCL, pH 4.5 buffer and pH 6.8 buffer).

As described above, the aim of the invention is to make a highly soluble active compound available uniformly over hours. The solution to this problem has surprisingly been made possible by the use of polymeric active compound excipients, where the latter slowly form a gel in the presence of physiological fluids, such as saliva or gastric or intestinal juice, and release the active compound from the tablet matrix slowly and in a controlled manner by diffusion.

A solution is provided here by polyvinyl alcohols (PVAs), which, as synthetic polymers, are water-soluble resins and have excellent film-forming and emulsifying properties and form a gel in aqueous solutions. According to USP, PVAs are characterised by the formula $(C_2H_4O)_n$ in which n denotes an integer in the range from 500 to 5,000. Depending on the molecular size of these polymers and their chemical composition, their properties vary greatly, in particular with respect to the water solubility, but also in relation to the tabletability.

PVAs are prepared from polyvinyl acetate, with some or all of the functional acetate groups being hydrolysed in order to obtain functional alcohol groups. The solubility of the polymer in aqueous media increases with the degree of hydrolysis, but the crystallinity and melting point of the polymer also increase. In addition, the glass transition temperature varies depending on the degree of hydrolysis.

For example, a 38% hydrolysed material does not have a melting point, but has a glass transition temperature of about 48° C., whereas a 75% hydrolysed material has a melting point of about 178° C., an 88% hydrolysed material has a melting point of about 196° C. and a 99% hydrolysed material has a melting point of about 220° C., but the polymer tends to decompose rapidly at a temperature above 200° C.

For the preparation of the compositions according to the invention, use can be made of polyvinyl alcohols (PVAs) of grades 18-88, 26-88 and 40-88 and all grades in between, including grade 28-99 in accordance with JPE and Ph. Eur.

Although polyvinyl alcohols are soluble in water, they are virtually insoluble in almost all organic solvents, with the exception of a few solvents, such as, for example, in ethanol with low solubility. These properties of the polymers make it very difficult to prepare tablet formulations which comprise a high proportion of PVAs and which are directly tabletable.

For use in pharmaceutical formulations, polyvinyl alcohols of different degrees of hydrolysis are specified in the various pharmacopoeia.

The European Pharmacopoeia prescribes that a permissible polyvinyl alcohol for use in pharmaceutical doses must have an ester value of not greater than 280 and an average relative molecular weight between 20,000 and 150,000. The percentage of hydrolysis (H) can be calculated from the following equation:

$H = ((100 - (0.1535)(EV))/(100 - (0.0749)(EV))) \times 100$, where EV corresponds to the ester value of the polymer. The ester value means the quantity of potassium hydroxide in mg required to saponify the esters in 1 g of sample. The ester value is calculated from the difference between the saponification value and the acid value.

Thus, according to the monograph in the European Pharmacopoeia, only PVA polymers having a percentage hydrolysis of greater than 72.2% can be employed.

According to the United States Pharmacopeia, polyvinyl alcohols which are suitable for use in pharmaceutical administration forms must have a percentage degree of hydrolysis of between 85 and 89% and a degree of polymerisation of 500 to 5,000. The degree of polymerisation (DM) is calculated by the equation:

$DM = (\text{molar mass})/((86) - (0.42(\text{the degree of hydrolysis})))$

A PVA which can be employed in pharmaceutical formulations in accordance with the European Pharmacopoeia monograph is a PVA having a degree of hydrolysis of between 72.2% and 90%, which covers both PVAs in accordance with the Ph. Eur. (hydrolysis of more than 72.2%, but less than 90%, and also those in accordance with the USP (degree of hydrolysis between 85-89%). These PVA grades have a molecular weight in the range from 14,000 g/mol to 250,000 g/mol.

Experiments have now shown that it is not only the degree of hydrolysis of the polyvinyl alcohols employed, and thus the crystallinity, that plays a role for good processability in tablet formulations, but also the physical properties and appearance forms of the commercial PVA grades employed.

As has already been indicated above, polyvinyl alcohols having a correspondingly high degree of hydrolysis are only directly tabletable under particular conditions, i.e. granulation steps have to be carried out in advance or the PVAs employed must be mixed with further tableting aids and easily compressible binders, so that the proportion of polyvinyl alcohol in the composition as a whole is reduced.

Experiments have surprisingly now shown that particularly fine-grained polyvinyl alcohols can be made accessible to direct tabletability. Correspondingly fine-grained polyvinyl alcohols can be obtained if suitable polyvinyl alcohols which have been certified for use in pharmaceutical formulations are ground and sieved.

In this way, it is possible to prepare directly tabletable mixtures comprising PVA powder in which the content of PVAs can be set surprisingly high.

The experiments carried out have also shown that the tabletability of the polyvinyl alcohols pretreated in this way can be improved further by combining them in a suitable manner with further polymeric assistants. This means that the ground, fine-grained powders can subsequently be combined with further, suitable polymeric assistants, causing the compressibility of the co-mixture obtained to be improved still further.

It has been found here that particularly readily tabletable combinations are obtained if the ground, fine-grained polyvinyl alcohols are mixed with microcrystalline celluloses. To this end, use can be made of commercially available, microcrystalline celluloses which have been certified for use in pharmaceutical formulations, such as, for example, the grades Vivapur® 102 and Emcocel® from JRS Pharma and the grade Avicel® PH 102 from FMC Biopolymer. In particular if the microcrystalline celluloses used are particularly fine-grained, a considerably improved compressibility of the co-mixtures is evident.

This is of particular importance for the development of directly compressible retard tablets, since the pharmaceutical formulation scientist is always in need of even "better assistants", i.e. matrices having further-improved compressibilities. This is due to the fact that it is an aim to be able to process even extremely poorly compressible APIs in a direct tableting process, which, however, does not succeed with the DC material of lower compressibility.

In addition, on use of a directly compressible tableting matrix having improved compressibility, its use amount can be reduced, enabling the production of tablets of lower weight and reduced dimensions, where the tablets obtained also furthermore have very good tablet hardnesses (so-called "dilution effect"). These properties are interesting, in particular, for so-called "high-dose" retard tablets, since the reduced tablet dimensions improve swallowing by the patient here and thus ensure compliance and consequently therapeutic success.

Surprisingly, the experiments in the testing of the tabletability of ground PVA grades with various microcrystalline celluloses (MCCs) have shown that an impairment or alternatively an improvement in the compressibility can occur, depending on the MCC grade used. In particular, the grades Avicel PH105, Vivapur 101 and Avicel PH101 cause a significant increase in the tablet hardnesses compared with other MCC grades—at the same pressing forces. More detailed investigations of these MCC grades have shown that they differ from the other grades through their particle sizes. The particle size of these MCCs are preferably in the $D_{v50}$ range: 17-67 µm. It has been found that the finer the MCC particle size, the better tablet hardnesses are achieved in combination with fine-grained PVAs. The MCC grades having particle sizes as far as possible smaller than 100 µm should therefore preferably be used for the preparation of the co-mixtures according to the invention, particularly preferably those having average particle sizes smaller than 70 µm, especially preferably smaller than 20 µm, measured as $D_{v50}$ by laser diffraction. On use of "coarser-grained" MCCs (from 100 µm and in particular from 180 µm), by contrast, the tablet hardnesses drop significantly.

It has been found to be particularly surprising in this connection that very apparently only the MCCs are suitable for achieving these improved direct compression properties; other excipients which usually promote direct compression, such as, for example, directly compressible calcium hydrogen phosphates, including Fujicalins® (Fuji Chemical Industry, Japan), directly compressible sorbitols (for example Parteck® SI 400, Merck KGaA, Germany), directly compressible mannitols (for example Parteck® M200, Merck KGaA, Germany) or directly compressible starches (for example starch 1500, Colorcon Limited, UK), do not exhibit this effect in combination with PVAs and do not result in directly compressible powder mixtures with the PVAs, as our own investigations have shown.

This effect which has surprisingly been found enables the pharmaceutical formulation scientist now to be provided with a directly compressible premix, predominantly consisting of PVA and fine-grained microcrystalline cellulose, for the production of tablets which can result in acceleration of a development process of a new tablet formulation.

The improvement in the tablet hardnesses at a constant PVA/MCC ratio in the direct-compression matrix provides the formulation scientist with the possibility of also converting active compounds which hitherto could only be compressed with difficulty or not at all into a retard tablet. It is furthermore now also possible for him to convert high-dose APIs into a "patient-friendly" retard tablet having dimensions which can easily be swallowed. In addition, it is now possible, if required, to reduce the amount of microcrystalline cellulose for the same amount of PVA and thus to reduce the tablet weight and the tablet dimensions without changing the retardation effect of the PVA. These materials result in a better dissolution effect than comparative materials based on coarser-grained MCC grades.

Microcrystalline cellulose (MCC) is one of the most important tableting aids in the production of pharmaceuticals and is preferably employed as active compound excipient and is an essential component for oral dosage forms of virtually any type, such as tablets, capsules, sachets, granules and others. In pure form, microcrystalline cellulose (MCC) having the general formula $(C_6H_{10}O_5)_n$ is white, free-flowing cellulose in powder form which is commercially available with various particle sizes. In pharmaceutical grade, it meets the USP standards. Microcrystalline cellulose serves, inter alia, as indigestible, non-resorbable ballast substance for calorie-reduced foods, for example salad dressings, desserts and ice creams, as release agent or as excipient. As stated in the above description, it is used in pharmacy as a binder or excipient for the production of tablets. In this connection, it has proven particularly suitable for direct tableting and results in hard tablets which have short disintegration times given suitable formulation.

MCC is obtained from woody plant parts (not from waste paper). Plant cellulose is freed from non-crystalline cellulose components using dilute hydrochloric acid at temperatures above 100° C. This means that pharmaceutical grade MCC can be obtained by partial hydrolysis of highly pure cellulose and subsequent purification and drying. The hydrolysis can optionally be followed by carboxylation in order to improve the hydrophilic properties.

MCC is insoluble in water, alcohols and organic solvents. In water, MCC forms a three-dimensional matrix consisting of innumerable, insoluble microcrystals, which form a stable thixotropic gel. The advantageous properties of MCC are also retained in the case of temperature-induced changes in the phase state, for example on transition into the frozen state or on heating to elevated temperatures, meaning that MCC is particularly highly suitable for ready mixes for further processing.

Suitable MCCs for achieving adequate tablet hardnesses have proven to be the commercially available grades which have average particle sizes $D_{v50}$ if possible less than 100 µm, preferably less than 70 µm, particularly preferably in the $D_{v50}$ range: 17-67 µm, especially preferably less than 20 µm, measured as $D_{v50}$ by laser diffraction. Fine-grained MCC grades of this type preferably have bulk densities in the range from 0.20 to 0.35 g/cm$^3$, preferably in the range from 0.20 to 0.31 g/cm$^3$. Suitable commercially available MCC grades which meet these criteria and have been qualified for use in pharmaceutical formulations are, for example, Vivapur 101 (dried in a stream of air, average particle size $D_{v50}$ 65 µm, determined by laser diffraction, bulk density 0.26-0.31 g/cm$^3$), Avicel PH 101 (average particle size 50 µm, bulk density 0.26-0.31 g/cm$^3$) and Avicel PH 105 (spray-dried, average particle size $D_{v50}$ 20 µm, determined by laser diffraction, bulk density 0.20-0.30 g/cm$^3$).

However, other commercial products not mentioned here which meet the requirements described can also be used in accordance with the invention described here.

It is particularly surprising that combination of suitable microcrystalline celluloses with various PVA grades, in particular with PVAs having a very wide variety of viscosities, gives directly compressible mixtures which, if necessary, consist predominantly of PVAs, but optionally also of equal proportions of PVAs and microcrystalline celluloses. If desired, however, it is also possible to employ mixtures in which the proportion of the fine-grained microcrystalline celluloses is higher than that of the fine-grained polyvinyl alcohols.

It has proven particularly advantageous for the ratio of the fine-grained polyvinyl alcohols and fine-grained microcrystalline celluloses described in the compositions according to the invention to be in the range 5:1 to 1:5, based on the weight, preferably in a ratio in the range from 2:1 to 1:2, especially preferably in a ratio in the region of 1:1. Such co-mixtures have proven particularly suitable for the production of tablets having delayed release of active compound. After intensive mixing, the co-mixtures found here of PVA with MCCs have bulk densities in the range 0.38-0.48 g/ml with tapped densities in the range 0.53-0.65 g/ml.

The advantageous properties described of the combinations of fine-grained polyvinyl alcohols and fine-grained microcrystalline celluloses provide the formulation scientist in the pharmaceutical industry, but also in the food industry or in other technical areas, with a material which significantly simplifies the development effort for solid compressed administration forms having extended release of active compound. He needs only mix his active compound to be retarded with the PVA/MCC combination according to the invention, optionally add a few assistants, in particular lubricants, and then compress this mixture in a tableting machine. The particularly good tableting properties of this matrix have also facilitated the development of retard tablets with active compounds which per se are actually not regarded as directly compressible and had to be granulated in advance in processes carried out in a conventional manner. The use of this PVA/MCC matrix saves development time, investment in equipment and results in improved process reliability in development and production.

An advantageous side effect arises on use of the co-mixtures according to the invention in the tableting process, which consists in that the mixtures according to the invention result in comparatively low ejection forces, enabling significantly smaller amounts of lubricants to be used than is otherwise usual in tableting. Thus, instead of the usual addition of 1% of magnesium stearate, only about a quarter of this amount is required, in some cases even less. Under particular conditions, the addition of such lubricants can also be omitted entirely. This causes an additional improvement in the interparticular binding forces, i.e. harder tablets are obtained for the same pressing force, enabling reproducible release of active compound to be achieved. The latter is due to the fact that the release is essentially controlled via the PVA content, and the addition of a small amount of hydrophobic magnesium stearate only exerts a slight influence on the release behaviour.

Furthermore, the present invention relates to a process for influencing the tableting properties of fine-grained PVA grades, in particular of ground PVAs, which have per se only low compressibilities. Experiments have shown that these fine-grained PVAs can be converted into a directly compressible form by combination with fine-grained MCCs.

Fine-grained PVAs are particularly suitable for use as retardation matrices, since they can generally be employed very well in order to prepare more homogeneous mixtures with the active compound to be retarded. The latter is of particular importance for the single dosage accuracy "content uniformity" in order always to obtain the same amount of active compound in each individual tablet.

In addition, this type of formulation with fine-grained PVA grades has the advantage that the large surface areas of the fine PVA particles results in more homogeneous gel layer formation after moistening in the gastrointestinal tract, which, when the tablets have been taken by the patient, results in more reproducible and possibly also extended diffusion of the active compound through this gel.

Procedure

For the preparation of the co-mixtures according to the invention, finely ground polyvinyl alcohols (PVAs) are mixed intensively with selected fine-grained microcrystalline celluloses (MCCs) and thus converted into co-mixtures which are eminently suitable as directly compressible tableting matrices. This is particularly surprising since blends of such PVAs with other directly tabletable assistants—also very readily compressible per se—on the market do not exhibit this direct compression effect with the pulverulent PVAs, in particular also not with any desired microcrystalline celluloses. Only when fine-grained PVAs are combined with particularly fine-grained microcrystalline celluloses are directly compressible co-mixtures obtained.

With these fine-grained co-mixtures according to the invention, active compounds which are poorly compressible per se can advantageously be converted into formulations which can very readily be compressed to give tablets without further preparations. Furthermore, it can be shown with the tablets produced which comprise corresponding co-mixtures as active compound excipient, that the active compound can be released in a controlled manner over a very long time from tablets produced in this way. The corresponding active compound-containing tablets exhibit delayed releases of active compound of at least 2 hours, preferably of over at least 6 hours, particularly preferably of at least 8 hours, especially preferably of at least 10 hours, and very particularly preferably releases of active compound of up to 12 hours, depending on the active compound employed and on the mixing ratio of the fine-grained polyvinyl alcohols with the microcrystalline celluloses.

Since the term "directly compressible" is not defined in a binding manner in connection with the preparation of tablet formulations, the pressing behaviour of a commercial as very readily compressible mannitol (Parteck® M 200 (mannitol), suitable for use as excipient EMPROVE® exp Ph. Eur, BP, JP, USP, E 421, Article No. 1.00419, Merck KGaA, Darmstadt, Germany) is used in the present description as standard for comparison. The aim is to come as close as possible to the behaviour of Parteck® M 200 with respect to its compressibility by means of the directly compressible co-mixtures which comprise fine-grained PVAs with fine-grained microcrystalline celluloses in relatively large amount.

The experiments carried out have shown that active compound-containing tablets which comprise a composition according to the invention in the form of a co-mixture in an amount of 1-99% by weight, preferably in an amount of 5-95% by weight, very particularly preferably in an amount of 10-90% by weight, based on the total weight of the tablet, have the desired, particularly good compressibility. Tablets having particularly high tablet hardnesses which require surprisingly low ejection forces in the production process can advantageously be obtained with such compositions as desired even on use of low pressing forces. Even on use of a pressing force of 20 kN, tablets having a tablet hardness of up to 462 N are obtained which only require an ejection force of less than 60 N. In addition, these tablets have only low friabilities, as can be shown by suitable experiments.

The present invention thus provides a process for the preparation of directly compressible compositions having extended release of active compound and particularly good compressibility, giving a co-mixture of fine-grained microcrystalline celluloses (MCCs) and fine-grained polyvinyl alcohols (PVAs) in which polyvinyl alcohol is ground to give a fine-grained powder having an average particle size $D_{v50}$ in the range from 50 to 260 µm, a bulk density in the range from 0.55 to 0.62 g/ml and an angle of repose in the range from 35 to 38° and is sieved through an 800 µm sieve, and the powder obtained is mixed with fine-grained microcrystalline celluloses (MCCs) having an average particle size $D_{v50}$ in the region <100 µm, preferably having average particle sizes of $D_{v50}$<70 µm, particularly preferably having average particle sizes in the $D_{v50}$ range 17 to 67 µm, in particular in the $D_{v50}$ range 17 µm-20 µm, and having bulk densities in the range from 0.20 to 0.35 g/cm³, preferably in the range from 0.20 to 0.31 g/cm³. In this way, a directly compressible co-mixture is obtained, to which various active compounds can be added if desired and which can be compressed to give tablets having delayed release of active compound.

The examples given below disclose methods and conditions for the preparation of PVA/MCC co-mixtures according to the invention. It is self-evident to the person skilled in the art in the area that other methods for grinding and mixing the starting substances than described here are also available.

The examples demonstrate the particular advantages of these fine-grained PVA/MCC combinations compared with the inadequate compressibilities obtained by PVA combinations with other excipients—but ones which are regarded as particularly readily tabletable.

On blending a fine-grained PVA/MCC matrix according to the invention with a pulverulent active compound which is poorly compressible per se and addition of a very small amount of magnesium stearate as lubricant, tablets of adequate hardnesses with low mechanical abrasion can be obtained by simple direct tableting and are readily available for further treatment, for example for packaging in blister packs or for break-free removal from these blister packs by the patient. Corresponding active compound-containing tablets show that extended release of active compound from such PVA/MCC matrix tablets over several hours can be guaranteed.

BRIEF DESCRIPTION OF THE DRAWINGS

FIG. 1: pressing force/tablet hardness profile (from Table 1b)

FIG. 2: pressing force/tablet hardness profile (from Table 2b)

FIG. 3: pressing force/tablet hardness profile (from Table 3b)

FIG. 4: pressing force/tablet hardness profile (from Table 4b)

EXAMPLES

Figure 1:
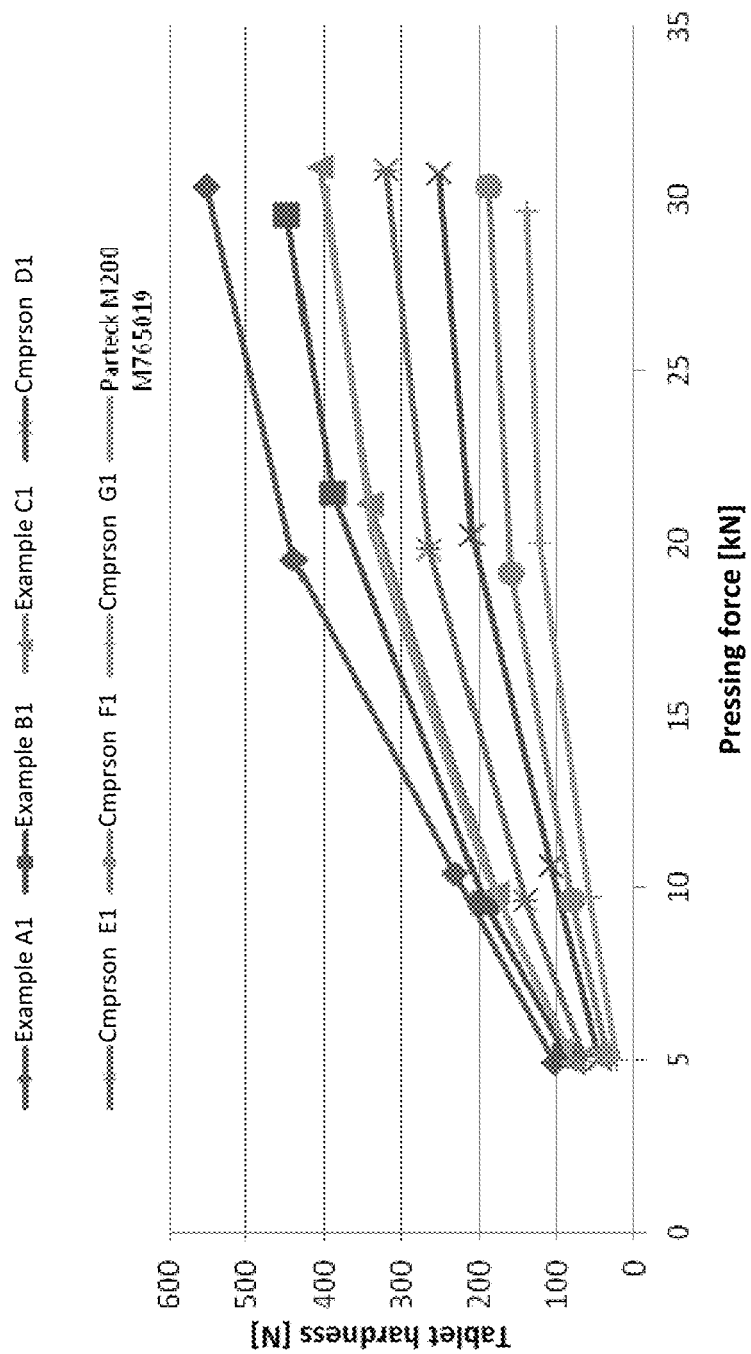
FIGS. 1 to 4 show graphically the experimental results for illustration.

The present description enables the person skilled in the art to apply the invention comprehensively. Even without further comments, it is therefore assumed that a person skilled in the art will be able to utilise the above description in the broadest scope.

If anything is unclear, it goes without saying that the publications and patent literature cited should be consulted. Accordingly, these documents are regarded as part of the disclosure content of the present description.

For better understanding of the invention and in order to illustrate it, examples are given below which are within the scope of protection of the present invention. These examples also serve to illustrate possible variants. Owing to the general validity of the inventive principle described, however, the examples are not suitable for reducing the scope of protection of the present application to these alone.

Furthermore, it goes without saying to the person skilled in the art that, both in the examples given and also in the remainder of the description, the component amounts present in the compositions always only add up to 100% by weight or mol-%, based on the composition as a whole, and cannot exceed this, even if higher values could arise from the percent ranges indicated. Unless indicated otherwise, % data are thus regarded as % by weight or mol-%, with the exception of ratios, which are reproduced in volume figures.

The temperatures given in the examples and the description as well as in the claims are in ° C.

The conditions for the preparation of the specific PVA/MCC combination according to the invention arise from the various examples. The MCC grades Avicel PH105 (Examples A1-A4) and Avicel PH101 (Examples C1-C4) from FMC Biopolymer and the grade Vivapur 101 (Examples B1-B4) from JRS Pharma are very particularly suitable. With these materials, the hardest tablets are obtained on use of comparable pressing forces, i.e these specific combinations exhibit the best "dilution" potential.

Characterisation of the Materials Used

1. PVA Grade Used and their Properties:
1.1 Raw Materials for Grinding
1.1.1. PVA 4-88: polyvinyl alcohol 4-88, suitable for use as excipient EMPROVE® exp Ph. Eur., USP, JPE, Article No. 1.41350, Merck KGaA, Darmstadt, Germany
1.1.2. PVA 18-88: polyvinyl alcohol 18-88, suitable for use as excipient EMPROVE® exp Ph. Eur., USP, JPE, Article No. 1.41355, Merck KGaA, Darmstadt, Germany
1.1.3. PVA 26-88: polyvinyl alcohol 26-88, suitable for use as excipient EMPROVE® exp Ph. Eur., USP, JPE, Article No. 1.41352, Merck KGaA, Darmstadt, Germany
1.1.4. PVA 40-88: polyvinyl alcohol 40-88, suitable for use as excipient EMPROVE® exp Ph. Eur., USP, JPE, Article No. 1.41353, Merck KGaA, Darmstadt, Germany
1.1.5. PVA 28-99: polyvinyl alcohol 28-99, suitable for use as excipient EMPROVE® exp JPE, Article No. 1.41356, Merck KGaA, Darmstadt, Germany These PVA grades are in the form of coarse particles—having a size of several millimetres—which in this form cannot be employed as a directly compressible tableting matrix.

The large particles do not allow reproducible filling of the dies and thus also do not allow a constant tablet weight at high rotational speeds of the (rotary) tableting machines. In addition, only fine-grained PVAs are able to ensure homogeneous distribution of the active compound without the occurrence of separation effects in the tablets. This is absolutely necessary for ensuring individual dosage accuracy of the active compound (content uniformity) in each tablet produced. In addition, only a fine-grained PVA can also ensure the homogeneous gel formation throughout the tablet body that is necessary for reproducible retardation.

For these reasons, the above-mentioned coarse-grained PVA grades must be comminuted, i.e. ground, before use as directly compressible retardation matrices.

1.2 Ground PVA Grades
1.2.1. Ground PVA 4-88, from polyvinyl alcohol 4-88 Article No. 1.41350
1.2.2. Ground PVA 18-88, from polyvinyl alcohol 18-88 Article No. 1.41355
1.2.3. Ground PVA 26-88, from polyvinyl alcohol 26-88 Article No. 1.41352
1.2.4. Ground PVA 40-88, from polyvinyl alcohol 40-88 Article No. 1.41353
1.2.5. Ground PVA 28-99, from polyvinyl alcohol 28-99 Article No. 1.41356

Grinding:

The grinding of the PVA grades is carried out in an Aeroplex 200 AS spiral jet mill from Hosokawa Alpine, Augsburg, Germany, under liquid nitrogen as cold grinding from 0° C. to minus 30° C., The resultant product properties of the ground PVA grades, in particular the powder characteristics, such as bulk density, tapped density, angle of repose, BET surface area, BET pore volume and the particle size distributions, are evident from the following tables:

Bulk Density, Tapped Density, Angle of Repose, BET Surface Area, BET Pore Volume:

(details on the measurement method, see under Methods)

| Sample | Bulk density (g/ml) | Tapped density (g/ml) | Angle of repose (°) | BET surface area (m²/g) | BET pore volume (cm³/g) |
| --- | --- | --- | --- | --- | --- |
| PVA 4-88* | 0.61 | 0.82 | 35.1 | 0.1308 | 0.0008 |
| PVA 18-88* | 0.57 | 0.76 | 35.5 | 0.1831 | 0.0011 |
| PVA 26-88* | 0.56 | 0.74 | 35.5 | 0.2045 | 0.0013 |
| PVA 40-88* | 0.59 | 0.77 | 36.9 | 0.1123 | 0.0009 |
| PVA 28-99* | 0.58 | 0.76 | 37.7 | 0.2210 | 0.0016 |

*ground PVA

Particle Distribution Determined by Laser Diffraction with Dry Dispersal (1 Bar Counterpressure):

figures in μm (details on the measurement method, see under Methods)

| Sample | Dv5 | Dv10 | Dv20 | Dv25 | Dv30 | Dv50 | Dv75 | Dv90 |
| --- | --- | --- | --- | --- | --- | --- | --- | --- |
| PVA 4-88* | 21.36 | 33.93 | 60.39 | 75.25 | 91.61 | 177.74 | 380.57 | 790.37 |
| PVA 18-88* | 29.67 | 44.93 | 73.95 | 89.11 | 105.22 | 185.49 | 375.88 | 755.84 |
| PVA 26-88* | 27.76 | 42.32 | 73.01 | 90.14 | 108.67 | 198.51 | 382.65 | 676.96 |
| PVA 40-88* | 31.84 | 50.64 | 89.13 | 109.77 | 131.45 | 230.52 | 413.71 | 634.59 |
| PVA 28-99* | 24.87 | 39.81 | 72.81 | 90.72 | 109.31 | 191.42 | 343.54 | 561.23 |

*ground PVA

Particle Distribution Determined by Laser Diffraction with
Dry Dispersal (2 Bar Counterpressure):
figures in μm (details on the measurement method, see
under Methods)

| Sample | Dv5 | Dv10 | Dv20 | Dv25 | Dv30 | Dv50 | Dv75 | Dv90 |
|---|---|---|---|---|---|---|---|---|
| PVA 4-88* | 19.09 | 30.21 | 52.69 | 64.83 | 77.87 | 143.83 | 279.64 | 451.94 |
| PVA 18-88* | 26.90 | 40.38 | 65.3 | 78.08 | 91.55 | 159.10 | 321.46 | 607.64 |
| PVA 26-88* | 24.59 | 36.93 | 61.67 | 75.05 | 89.33 | 157.79 | 286.17 | 434.23 |
| PVA 40-88* | 31.03 | 49.47 | 88.54 | 110.06 | 132.79 | 235.87 | 430.35 | 686.1 |
| PVA 28-99* | 24.27 | 39.63 | 74.31 | 93.13 | 112.51 | 196.45 | 350.21 | 570.12 |

*ground PVA

Particle Distribution Determined by Laser Diffraction with
Dry Dispersal (3 Bar Counterpressure):
figures in μm (details on the measurement method, see
under Methods)

| Sample | Dv5 | Dv10 | Dv20 | Dv25 | Dv30 | Dv50 | Dv75 | Dv90 |
|---|---|---|---|---|---|---|---|---|
| PVA 4-88* | 18.35 | 29.27 | 51.25 | 63.09 | 75.77 | 139.46 | 269.8 | 425.62 |
| PVA 18-88* | 24.55 | 36.60 | 57.91 | 68.48 | 79.45 | 132.37 | 246.56 | 393.59 |
| PVA 26-88* | 25.17 | 38.18 | 64.35 | 78.47 | 93.57 | 167.41 | 317.16 | 514.18 |
| PVA 40-88* | 32.81 | 53.33 | 96.27 | 119.61 | 144.21 | 256.31 | 463.67 | 717.76 |
| PVA 28-99* | 22.33 | 35.92 | 65.94 | 82.31 | 99.37 | 174.84 | 305.5 | 454.03 |

*ground PVA

Particle Distribution Determined by Laser Diffraction with
Wet Dispersal (in Low-Viscosity Silicone Oil):
figures in μm (details on the measurement method, see
under Methods)

| Muster | Dv5 | Dv10 | Dv20 | Dv25 | Dv30 | Dv50 | Dv75 | Dv90 |
|---|---|---|---|---|---|---|---|---|
| PVA 4-88* | 10.03 | 20.1 | 38.02 | 47.82 | 58.31 | 110.91 | 231.64 | 390.95 |
| PVA 18-88* | 17.19 | 30.25 | 50.06 | 59.22 | 68.47 | 111.89 | 212.70 | 357.70 |
| PVA 26-88* | 15.42 | 26.76 | 45.50 | 54.83 | 64.47 | 110.50 | 212.91 | 353.68 |
| PVA 40-88* | 20.41 | 34.80 | 60.35 | 73.32 | 86.96 | 154.96 | 299.57 | 490.08 |
| PVA 28-99* | 14.68 | 25.96 | 47.49 | 58.88 | 70.80 | 127.68 | 240.70 | 376.70 |

*ground PVA

Particle Distribution Determined by Tower Sieving:
figures in percent by weight (details on the measurement
method, see under Methods)

| Sample | <32 μm | 32-50 μm | 50-75 μm | 75-100 μm | 100-150 μm | 150-200 μm | 200-250 μm |
|---|---|---|---|---|---|---|---|
| PVA 4-88* | 3.3 | 7.9 | 12.6 | 12.2 | 19.6 | 12.9 | 10.5 |
| PVA 18-88* | 0.5 | 8.1 | 12.8 | 13.6 | 20.4 | 15.0 | 9.4 |
| PVA 26-88* | 5.3 | 8.4 | 12.3 | 13.6 | 21.8 | 13.1 | 9.0 |
| PVA 40-88 | 2.6 | 5.5 | 8.1 | 8.8 | 17.8 | 14.0 | 10.7 |
| PVA 28-99* | 5.0 | 7.1 | 9.1 | 9.8 | 20.4 | 13.2 | 11.7 |

| Sample | 250-300 μm | 300-355 μm | 355-400 μm | 400-500 μm | 500-600 μm | 600-710 μm | >710 μm |
|---|---|---|---|---|---|---|---|
| PVA 4-88* | 6.5 | 4.5 | 2.8 | 3.5 | 2.0 | 0.9 | 0.8 |
| PVA 18-88* | 5.8 | 4.2 | 2.6 | 3.5 | 2.1 | 1.0 | 1.0 |
| PVA 26-88* | 5.0 | 3.7 | 2.2 | 2.7 | 1.8 | 0.6 | 0.5 |
| PVA 40-88 | 7.5 | 6.6 | 3.9 | 5.9 | 4.1 | 1.9 | 2.6 |
| PVA 28-99* | 7.9 | 5.3 | 3.2 | 3.7 | 2.0 | 0.8 | 0.8 |

*ground PVA

2. Microcrystalline Celluloses (MCCs) the Preparation of the Blends with Polyvinyl Alcohols (Ground)

2.1 Avicel® PH 101, microcrystalline cellulose, Ph. Eur., NF, JP, FMC BioPolymer, USA
2.2 Avicel® PH 102, microcrystalline cellulose, Ph. Eur., NF, JP, FMC BioPolymer, USA
2.3 Avicel® PH 102 SCG, microcrystalline cellulose, Ph. Eur., NF, JP, FMC BioPolymer, USA
2.4 Avicel® PH 105, microcrystalline cellulose, Ph. Eur., NF, JP, FMC BioPolymer, USA
2.5 Vivapur® Type 12, microcrystalline cellulose, Ph. Eur., NF, JP, JRS Pharma, Rosenberg, Germany
2.6 Vivapur® Type 101, microcrystalline cellulose, Ph. Eur., NF, JP, JRS Pharma, Rosenberg, Germany
2.7 Vivapur® Type 102 Premium, microcrystalline cellulose, Ph. Eur., NF, JP, JRS Pharma, Rosenberg, Germany
2.8 Vivapur® Type 200, microcrystalline cellulose, Ph. Eur., NF, JP, JRS Pharma, Rosenberg, Germany
2.9 Emcocel® 90 M, microcrystalline cellulose, Ph. Eur., NF, JP, JRS Pharma, Rosenberg, Germany
2.10 Emcocel® LP 200, microcrystalline cellulose, Ph. Eur., NF, JP, JRS Pharma, Rosenberg, Germany
2.11 Comprecel® M 302, microcrystalline cellulose, Ph. Eur., NF, JP, BP, USP, Mingtai Chemical Co. Ltd., Taiwan Particle Distribution Determined by Laser Diffraction with Dry Dispersal (1 Bar Counterpressure):
figures in µm (details on the measurement method, see under Methods)

| Sample | Dv10 | Dv20 | Dv25 | Dv30 | Dv50 | Dv75 | Dv90 |
|---|---|---|---|---|---|---|---|
| Avicel ® PH 101 | 22.59 | 33.09 | 37.77 | 42.36 | 61.82 | 98.62 | 161.34 |
| Avicel ® PH 102 | 28.27 | 46.75 | 56.59 | 66.56 | 107.27 | 170.38 | 235.70 |
| Avicel ® PH 102 SCG | 48.99 | 90.03 | 106.32 | 120.84 | 173.66 | 251.80 | 331.64 |
| Avicel ® PH 105 | 6.80 | 10.21 | 11.61 | 12.94 | 18.50 | 28.35 | 40.38 |
| Vivapur ® 12 | 42.55 | 75.61 | 92.59 | 108.97 | 171.37 | 264.07 | 358.09 |
| Vivapur ® 101 | 20.66 | 30.70 | 35.97 | 41.53 | 66.58 | 108.89 | 155.53 |
| Vivapur ® 102 | 31.56 | 53.04 | 66.00 | 79.89 | 135.87 | 215.53 | 293.94 |
| Vivapur ® 200 | 49.25 | 97.09 | 125.64 | 152.47 | 245.21 | 375.17 | 507.15 |
| Emcocel ® 90M | 41.28 | 63.99 | 73.89 | 83.41 | 121.96 | 185.25 | 253.79 |
| Emcocel ® LP 200 | 68.47 | 113.69 | 129.77 | 144.39 | 199.67 | 285.27 | 376.22 |
| Comprecel ® M 302 | 30.07 | 55.56 | 66.85 | 77.23 | 116.30 | 176.60 | 240.36 |

Particle Distribution Determined by Laser Diffraction with Dry Dispersal (2 Bar Counterpressure):
figures in µm (details on the measurement method, see under Methods)

| Sample | Dv10 | Dv20 | Dv25 | Dv30 | Dv50 | Dv75 | Dv90 |
|---|---|---|---|---|---|---|---|
| Avicel ® PH 101 | 19.43 | 28.55 | 32.60 | 36.53 | 52.81 | 80.77 | 114.13 |
| Avicel ® PH 102 | 28.40 | 47.32 | 57.45 | 67.69 | 108.91 | 171.94 | 236.64 |
| Avicel ® PH 102 SCG | 48.32 | 84.95 | 100.38 | 114.43 | 166.33 | 243.47 | 321.96 |
| Avicel ® PH 105 | 6.39 | 9.81 | 11.19 | 12.52 | 18.03 | 27.77 | 39.70 |
| Vivapur ® 12 | 35.98 | 62.68 | 77.81 | 93.33 | 155.79 | 249.72 | 345.23 |
| Vivapur ® 101 | 19.61 | 29.42 | 34.61 | 40.15 | 66.06 | 113.18 | 176.82 |
| Vivapur ® 102 | 27.55 | 45.97 | 57.41 | 70.40 | 127.29 | 208.92 | 288.93 |
| Vivapur ® 200 | 44.08 | 86.21 | 113.63 | 140.90 | 235.62 | 365.86 | 497.34 |
| Emcocel ® 90M | 37.39 | 58.75 | 68.08 | 77.03 | 113.34 | 173.41 | 239.37 |
| Emcocel ® LP 200 | 75.97 | 121.31 | 137.44 | 152.19 | 208.23 | 294.84 | 385.17 |
| Comprecel ® M 302 | 33.33 | 62.38 | 74.56 | 85.63 | 127.04 | 190.77 | 257.84 |

Particle Distribution Determined by Laser Diffraction with Dry Dispersal (3 Bar Counterpressure):

figures in μm (details on the measurement method, see under Methods)

| Sample | Dv10 | Dv20 | Dv25 | Dv30 | Dv50 | Dv75 | Dv90 |
|---|---|---|---|---|---|---|---|
| Avicel ® PH 101 | 18.03 | 26.91 | 30.91 | 34.81 | 51.16 | 80.11 | 117.89 |
| Avicel ® PH 102 | 24.28 | 40.18 | 49.21 | 58.86 | 100.25 | 164.22 | 229.95 |
| Avicel ® PH 102 SCG | 42.19 | 77.05 | 92.59 | 106.73 | 158.55 | 234.98 | 312.72 |
| Avicel ® PH 105 | 6.10 | 9.50 | 10.88 | 12.20 | 17.67 | 27.29 | 38.96 |
| Vivapur ® 12 | 31.65 | 54.13 | 67.50 | 81.98 | 144.53 | 240.48 | 338.01 |
| Vivapur ® 101 | 17.23 | 25.91 | 30.40 | 35.18 | 58.17 | 99.16 | 143.94 |
| Vivapur ® 102 | 23.61 | 38.84 | 48.19 | 59.22 | 114.76 | 198.37 | 278.99 |
| Vivapur ® 200 | 38.43 | 73.36 | 97.85 | 124.94 | 223.50 | 356.46 | 490.73 |
| Emcocel ® 90M | 34.07 | 55.25 | 64.57 | 73.49 | 109.27 | 167.95 | 232.86 |
| Emcocel ® LP 200 | 61.18 | 104.76 | 120.78 | 135.31 | 189.83 | 272.98 | 358.76 |
| Comprecel ® M 302 | 29.22 | 54.80 | 66.28 | 76.75 | 115.86 | 175.96 | 239.63 |

*ground PVA

Particle Distribution Determined by Laser Diffraction with Wet Dispersal (in Low-Viscosity silicone oil):

figures in μm (details on the measurement method, see under Methods)

| Sample | Dv10 | Dv20 | Dv25 | Dv30 | Dv50 | Dv75 | Dv90 |
|---|---|---|---|---|---|---|---|
| Avicel ® PH 101 | 20.66 | 32.85 | 38.18 | 43.31 | 63.99 | 98.56 | 140.53 |
| Avicel ® PH 102 | 26.92 | 46.05 | 55.55 | 64.77 | 101.48 | 161.28 | 227.07 |
| Avicel ® PH 102 SCG | 38.64 | 69.23 | 83.63 | 97.33 | 150.39 | 231.75 | 316.41 |
| Avicel ® PH 105 | 5.21 | 9.07 | 10.51 | 11.84 | 17.11 | 26.17 | 37.37 |
| Vivapur ® 12 | 31.45 | 55.34 | 67.86 | 80.26 | 132.04 | 219.78 | 316.04 |
| Vivapur ® 101 | 17.51 | 26.83 | 31.53 | 36.51 | 59.93 | 99.84 | 144.07 |
| Vivapur ® 102 | 28.28 | 47.27 | 58.07 | 69.46 | 119.03 | 200.35 | 285.42 |
| Vivapur ® 200 | 33.53 | 59.12 | 74.18 | 90.77 | 171.42 | 302.56 | 434.89 |
| Emcocel ® 90M | 35.68 | 58.96 | 68.77 | 78.12 | 116.55 | 183.76 | 261.39 |
| Emcocel ® LP 200 | 60.38 | 105.52 | 122.18 | 137.35 | 194.75 | 283.57 | 377.02 |
| Comprecel ® M 302 | 27.02 | 52.05 | 63.61 | 74.24 | 114.48 | 178.54 | 248.78 |

2. Other Materials

Since the term "directly compressible" is not defined in a binding manner, the pressing behaviour of a commercial very readily compressible mannitol is employed as standard:

Parteck® M 200 (mannitol), suitable for use as excipient EMPROVE® exp Ph. Eur., BP, JP, USP, E 421, Article No. 1.00419, Merck KGaA, Darmstadt, Germany The aim is to come as close as possible to the behaviour of Parteck® M 200 by means of the directly compressible PVAs, in particular with respect to their compressibility.

Equipment/Methods for Characterisation of the Substance Properties

1. Bulk density: in accordance with DIN EN ISO 60: 1999 (German version)
   quoted in "g/ml"

2. Tapped density: in accordance with DIN EN ISO 787-11: 1995 (German version)
   quoted in "g/ml"
3. Angle of repose: in accordance with DIN ISO 4324: 1983 (German version)
   quoted in "degrees"
4. Surface area determined in accordance with BET: evaluation and procedure in accordance with the literature "BET Surface Area by Nitrogen Absorption" by S. Brunauer et al. (Journal of American Chemical Society, 60, 9, 1983) instrument: ASAP 2420 Micromeritics Instrument Corporation (USA); nitrogen; sample weight: about 3.0000 g; heating: 50° C. (5 h); heating rate 3K/min; quoting of the arithmetic mean from three determinations
5. Particle size determination by laser diffraction with dry dispersal: Master-sizer 2000 with Scirocco 2000 dispersion unit (Malvern Instruments Ltd. UK), determinations at a counterpressure of 1 and 2 bar; Fraunhofer evaluation; dispersant RI: 1.000, obscuration limits: 0.0-10.0%, tray type: general purpose, background time: 7500 msec, measurement time: 7500 msec, procedure in accordance with ISO 13320-1 and the information in the technical manual and specifications from the instrument manufacturer; result given in % by vol.
6. Particle size determination by laser diffraction with wet dispersal: Master-sizer 2000 with Hydro 2000SM wet-dispersion unit (Malvern Instruments Ltd., UK); dispersion medium low-viscosity silicone oil (manufacturer: Evonic Goldschmidt GmbH, Germany; manufacturer's name: Tegiloxan3, manufacturer's article no.: 9000305); dispersant RI: 1.403; stirrer speed: 2500 rpm; tray type: general purpose; background time: 7500 msec; measurement time: 7500 msec; obscuration limits: 7.0-13.0%; procedure in accordance with ISO 13320-1 and the information in the technical manual and specifications from the instrument manufacturer; result given in % by vol.
   Procedure: the suspension cell is filled with the low-viscosity silicone oil, the sample is added in portions until the target obscuration range (7.0-13.0%) has been reached, and the measurement is started after a waiting time of 2 minutes.
7. Particle size determination by dry sieving via a sieve tower: Retsch AS 200 control, Retsch (Germany); amount of substance: about 110.00 g; sieving time: 30 minutes; amplitude intensity: 1 mm; interval: 5 seconds; analytical sieve with metal-wire fabric in accordance with DIN ISO 3310; mesh widths (in μm): 710, 600, 500, 400, 355, 300, 250, 200, 150, 100, 75, 50, 32; amount distribution per sieve fraction indicated in the tables as "% by weight of the sample weight":
8. The tableting tests are carried out as follows:
   The mixtures in accordance with the compositions indicated in the experimental part are mixed for 5 minutes in a sealed stainless-steel container (capacity: about 2 l, height: about 19.5 cm, diameter: about 12 cm outside dimension) in a laboratory tumble mixer (Turbula T2A, Willy A. Bachofen, Switzerland).
   The magnesium stearate employed is Parteck LUB MST (vegetable magnesium stearate) EMPROVE exp Ph. Eur., BP, JP, NF, FCC Article No. 1.00663 (Merck KGaA, Germany) which has been passed through a 250 μm sieve.
   The compression to give 500 mg tablets (11 mm punch, round, flat, with bevel edge) is carried out in a Korsch EK 0-DMS instrumented eccentric tableting machine (Korsch, Germany) with the Catman 5.0 evaluation system (Hottinger Baldwin Messtechnik—HBM, Germany).

Depending on the pressing force tested (nominal settings: ~5, ~10, ~20 and ~30 kN; the effectively measured actual values are indicated in the examples), at least 100 tablets are produced for evaluation of the pressing data and determination of the pharmaceutical formulation characteristic values.

Tablet Hardnesses, Diameters and Heights:
Erweka Multicheck 5.1 (Erweka, Germany); average data (arithmetic means) from in each case 20 tablet measurements per pressing force. The measurements are carried out one day after the tablet production.

Tablet Abrasion:
TA420 friability tester (Erweka, Germany); instrument parameters and performance of the measurements in accordance with Ph. Eur. $7^{th}$ Edition "Friability of Uncoated Tablets". The measurements are carried out one day after tablet production.

Tablet Weight:
Average value (arithmetic mean) from the weighing of 20 tablets per pressing force: Multicheck 5.1 (Erweka, Germany) with Sartorius CPA 64 balance (Sartorius, Germany). The measurements are carried out one day after tablet production.

Experimental Results

The experiments have shown that, in particular, only the co-mixtures with three specific microcrystalline celluloses (MCCs) result in good compressibility.

The experiments have also shown that apparently not all commercially available MCC grades exhibit an improvement in the compressibility in the co-mixtures with ground PVAs.

Since the turn "directly compressible" is not defined in a binding manner, the pressing behaviour of a commercial mannitol which as very readily compressible (Parteck® M 200 (mannitol)), suitable for use as excipient EMPROVE® exp Ph. Eur., BP, JP, USP, E 421, Catalogue No, 100419, Merck KGaA, Darmstadt, Germany) is set as standard. The aim is to come as close as possible to the behaviour of Parteck® M200 with the directly compressible PVAs (as co-mixtures), in particular with respect to their compressibility.

The experiments have shown that co-mixtures based on finely ground polyvinyl alcohols with the fine-grained microcrystalline celluloses, such as, for example, with the commercially available products Avicel PH 105 (Examples A1-A4), Vivapur 101 (Examples B1-B4) and Avicel PH101 (Examples C1-C4) have very particularly good compressibility. This compressibility is equivalent or even significantly better than that of Parteck® M200, which is regarded as particularly readily directly compressible.

These specific PVA/MCC co-mixtures are thus particularly highly suitable in direct tableting as matrices for the formulation of retard tablets in combination with active compounds which are poorly compressible per se.

Procedure:
1a.
Preparation of the blends consisting of the various commercial microcrystalline celluloses with the ground PVA grade 4-88
1b.
Pressing of these blends (with addition of 0.25% by weight of Parteck® LUB MST) and tablet characterisation with respect to the parameters tablet hardness, tablet weight, tablet height, tablet abrasion and ejection force necessary 2a.

Preparation of the blends consisting of the various commercial microcrystalline celluloses with the ground PVA grade 18-88

2b.

Pressing of these blends (with addition of 0.25% by weight of Parteck® LUB MST) and tablet characterisation with respect to the parameters tablet hardness, tablet weight, tablet height, tablet abrasion and ejection force necessary 3a.

Preparation of the blends consisting of the various commercial microcrystalline celluloses with the ground PVA grade 26-88

3b.

Pressing of these blends (with addition of 0.25% by weight of Parteck® LUB MST) and tablet characterisation with respect to the parameters tablet hardness, tablet weight, tablet height, tablet abrasion and ejection force necessary 4a.

Preparation of the blends consisting of the various commercial microcrystalline celluloses with the ground PVA grade 40-88

4b.

Pressing of these blends (with addition of 0.25% by weight of Parteck® LUB MST) and tablet characterisation with respect to the parameters tablet hardness, tablet weight, tablet height, tablet abrasion and ejection force necessary Experimental Results:

1a. Preparation of the Blends of the Directly Compressible Excipients with the Ground PVA Grade 4-88

General description: ground PVA 4-88 is passed through an 800 µm hand sieve in order to remove any coarse components and agglomerates. 300 g of this sieved product are weighed out into a 2 l Turbula mixing vessel, 300 g of the corresponding microcrystalline cellulose from Table 1a are added and mixed for 5 min. in a T2A Turbula mixer.

TABLE 1a

Composition of the co-mixtures of ground PVA 4-88 with microcrystalline celluloses

| Composition | 50% by weight of PVA | 50% by weight of MCC |
| --- | --- | --- |
| Example A1 | PVA 4-88* | Avicel ® PH 105 |
| Example B1 | PVA 4-88* | Vivapur ® 101 |
| Example C1 | PVA 4-88* | Avicel ® PH 101 |
| Comparison D1 | PVA 4-88* | Vivapur ® 12 |
| Comparison E1 | PVA 4-88* | Vivapur ® 102 Premium |
| Comparison F1 | PVA 4-88* | Vivapur ® 200 |
| Comparison G1 | PVA 4-88* | Emcocel ® LP200 |

*ground PVA

1b. Compression of these Blends and Tablet Characterisation

Gen. description: 1.25 g of magnesium stearate are added to in each case 498.75 g of the co-mixtures of Examples A1-C1 or Comparisons D1-G1 prepared above in a Turbula mixing vessel, the mixture is mixed again for 5 min. in a T2A Turbula mixer and tabletted in a Korsch EK 0-DMS eccentric press.

The comparison used is Parteck® M200 blended with 1% of Parteck® LUB MST. Note: compression of Parteck® M200 with less magnesium stearate is not possible owing to the very high ejection forces which otherwise result.

TABLE 1b

Tableting data of the co-mixtures of ground PVA 4-88 with microcrystalline celluloses Key:

A: Pressing force [kN]  B: Tablet hardness after 1 day [N]
C: Tablet weight [mg]   D: Tablet height [mm]
E: Abrasion [%]         F: Ejection force (N)

| | A | | B | C | D | E | F |
| --- | --- | --- | --- | --- | --- | --- | --- |
| | Nominal | Actual | | | | | |
| Example A1 | 5 | 4.9 | 102.7 | 498.6 | 5.4 | 0.24 | 103.3 |
| | 10 | 10.4 | 230.8 | 493.1 | 4.8 | 0 | 110.1 |
| | 20 | 19.5 | 439.4 | 486.6 | 4.4 | 0 | 70.4 |
| | 30 | 30.3 | 551.5 | 486.9 | 4.3 | 0 | 48.6 |
| Example B1 | 5 | 5.1 | 89.6 | 500.8 | 5.5 | 0.43 | 90.1 |
| | 10 | 9.5 | 192.7 | 500.4 | 4.9 | 0.16 | 94.6 |
| | 20 | 21.4 | 390.1 | 504.9 | 4.5 | 0.07 | 58.8 |
| | 30 | 29.5 | 447.6 | 504.3 | 4.4 | 0.07 | 51.2 |
| Example C1 | 5 | 4.9 | 77.9 | 495.1 | 5.6 | 0.69 | 96.8 |
| | 10 | 9.8 | 178.6 | 497.8 | 4.9 | 0.16 | 98.7 |
| | 20 | 21.1 | 340.5 | 501.6 | 4.5 | 0.06 | 61.7 |
| | 30 | 30.9 | 405.0 | 503.6 | 4.4 | 0.05 | 50.7 |
| Comparison D1 | 5 | 5.0 | 45.8 | 495.8 | 5.4 | 1.47 | 86.6 |
| | 10 | 10.6 | 107.0 | 500.5 | 4.9 | 0.27 | 97.5 |
| | 20 | 20.2 | 208.9 | 502.0 | 4.4 | 0.08 | 75.4 |
| | 30 | 30.7 | 250.8 | 502.4 | 4.4 | 0.07 | 66.4 |
| Comparison E1 | 5 | 5.1 | 65.2 | 501.3 | 5.5 | 0.55 | — |
| | 10 | 9.6 | 140.0 | 504.8 | 4.9 | 0.19 | 95.9 |
| | 20 | 19.8 | 264.8 | 503.9 | 4.5 | 0.10 | 65.4 |
| | 30 | 30.8 | 321.2 | 504.7 | 4.4 | 0.06 | 56.3 |
| Comparison F1 | 5 | 5.1 | 33.7 | 497.8 | 5.5 | 4.72 | 75.4 |
| | 10 | 9.6 | 81.2 | 502.1 | 5.0 | 0.59 | 85.7 |
| | 20 | 19.1 | 160.4 | 503.2 | 4.6 | 0.19 | 62.4 |
| | 30 | 30.3 | 188.8 | 502.2 | 4.5 | 0.14 | 53.9 |
| Comparison G1 | 5 | 5.0 | 22.4 | 493.4 | 5.7 | 47.34 | 82.0 |
| | 10 | 9.7 | 58.2 | 498.0 | 5.0 | 1.24 | 91.1 |
| | 20 | 20.0 | 121.6 | 500.4 | 4.6 | 0.25 | 63.8 |
| | 30 | 29.6 | 138.3 | 500.8 | 4.5 | 0.21 | 54.7 |
| Parteck ® M200 | 5 | 5.2 | 84.1 | 497.8 | 5.1 | 0.21 | 155.8 |
| | 10 | 10.7 | 196.5 | 500.6 | 4.6 | 0.17 | 306.0 |
| | 20 | 20.3 | 340.0 | 499.4 | 4.2 | 0.15 | 513.6 |
| | 30 | 30.0 | 396.7 | 498.3 | 4.0 | 0.16 | 647.6 |

FIG. 1 shows a graph of the very different pressing force/tablet hardness profiles for better illustration.

2a. Preparation of the Blends of the Directly Compressible Excipients with the Ground PVA Grade 18-88

General description: ground PVA 18-88 is passed through an 800 µm hand sieve in order to remove any coarse components and agglomerates. 300 g of this sieved product are weighed out into a 2 l Turbula mixing vessel, 300 g of the corresponding microcrystalline cellulose from Table 2a are added and mixed for 5 min. in a T2A Turbula mixer.

TABLE 2a

Composition of the co-mixtures of ground PVA 18-88 with microcrystalline celluloses

| Composition | 50% by weight of PVA | 50% by weight of MCC |
| --- | --- | --- |
| Example A2 | PVA 18-88* | Avicel ® PH 105 |
| Example B2 | PVA 18-88* | Vivapur ® 101 |
| Example C2 | PVA 18-88* | Avicel ® PH 101 |
| Comparison D2 | PVA 18-88* | Vivapur ® 12 |
| Comparison E2 | PVA 18-88* | Vivapur ® 102 Premium |
| Comparison F2 | PVA 18-88* | Vivapur ® 200 |
| Comparison G2 | PVA 18-88* | Emcocel ® LP200 |

*ground PVA

2b. Compression of these Blends and Tablet Characterisation

General Description:

1.25 g of magnesium stearate are added to in each case 498.75 g of the co-mixtures of Examples A2-C2 or Comparisons D2-G2 prepared above in a Turbula mixing vessel, the mixture is mixed again for 5 min. in a T2A Turbula mixer and tabletted in a Korsch EK 0-DMS eccentric press.

The comparison used is Parteck® M200 blended with 1% of Parteck® LUB MST. Note: compression of Parteck® M200 with less magnesium stearate is not possible owing to the very high ejection forces which otherwise result.

TABLE 2b

Tableting data of the co-mixtures of ground PVA 18-88 with microcrystalline celluloses Key:

A: Pressing force [kN]  B: Tablet hardness after 1 day [N]
C: Tablet weight [mg]   D: Tablet height [mm]
E: Abrasion [%]         F: Ejection force (N)

| | A | | B | C | D | E | F |
|---|---|---|---|---|---|---|---|
| | Nominal | Actual | | | | | |
| Example A2 | 5 | 5.6 | 120.0 | 501.1 | 5.4 | 0.08 | 107.2 |
| | 10 | 10.3 | 239.1 | 501.9 | 4.9 | 0 | 108.8 |
| | 20 | 20.5 | 465.5 | 502.2 | 4.5 | 0 | 69.5 |
| | 30 | 31.1 | 591.0 | 497.2 | 4.3 | 0 | 49.2 |
| Example B2 | 5 | 4.8 | 82.2 | 497.9 | 5.5 | 0.44 | 83.6 |
| | 10 | 9.4 | 184.2 | 497.3 | 4.9 | 0.12 | 89.4 |
| | 20 | 21.0 | 363.8 | 498.6 | 4.4 | 0.04 | 58.1 |
| | 30 | 30.5 | 448.5 | 500.9 | 4.3 | 0.02 | 49.4 |
| Example C2 | 5 | 5.1 | 73.0 | 497.5 | 5.4 | 0.59 | 92.6 |
| | 10 | 10.3 | 172.5 | 501.5 | 4.9 | 0.13 | 94.6 |
| | 20 | 19.6 | 311.5 | 503.7 | 4.5 | 0.05 | 66.1 |
| | 30 | 31.2 | 401.2 | 504.8 | 4.4 | 0.03 | 52.0 |
| Comparison D2 | 5 | 5.3 | 35.7 | 498.1 | 5.6 | 2.51 | 87.3 |
| | 10 | 9.8 | 98.2 | 502.2 | 4.9 | 0.25 | 95.7 |
| | 20 | 20.8 | 181.8 | 504.5 | 4.5 | 0.07 | 66.9 |
| | 30 | 31.5 | 218.8 | 504.5 | 4.4 | 0.02 | 57.8 |
| Comparison E2 | 5 | 5.5 | 66.7 | 498.6 | 5.4 | 0.45 | 91.6 |
| | 10 | 10.1 | 139.1 | 501.2 | 4.9 | 0.13 | 94.1 |
| | 20 | 20.8 | 264.3 | 503.8 | 4.5 | 0.06 | 66.6 |
| | 30 | 28.8 | 304.7 | 502.5 | 4.4 | 0.02 | 60.0 |
| Comparison F2 | 5 | 4.9 | 26.1 | 493.6 | 5.6 | 7.70 | 74.5 |
| | 10 | 9.8 | 70.8 | 499.7 | 5.0 | 0.61 | 86.4 |
| | 20 | 20.7 | 149.1 | 501.5 | 4.5 | 0.16 | 65.5 |
| | 30 | 29.8 | 176.1 | 502.5 | 4.5 | 0.12 | 59.5 |
| Comparison G2 | 5 | 5.4 | 18.9 | 495.4 | 5.7 | 100.0 | 83.0 |
| | 10 | 9.8 | 45.4 | 502.2 | 5.1 | 1.57 | 90.8 |
| | 20 | 19.2 | 104.2 | 504.1 | 4.6 | 0.22 | 69.1 |
| | 30 | 29.8 | 126.5 | 506.1 | 4.5 | 0.14 | 59.0 |
| Parteck ® M200 | 10 | 5.2 | 84.1 | 497.8 | 5.1 | 0.21 | 155.8 |
| | | 10.7 | 196.5 | 500.6 | 4.6 | 0.17 | 306.0 |
| | | 20.3 | 340.0 | 499.4 | 4.2 | 0.15 | 513.6 |
| | | 30.0 | 396.7 | 498.3 | 4.0 | 0.16 | 647.6 |

Figure 2:
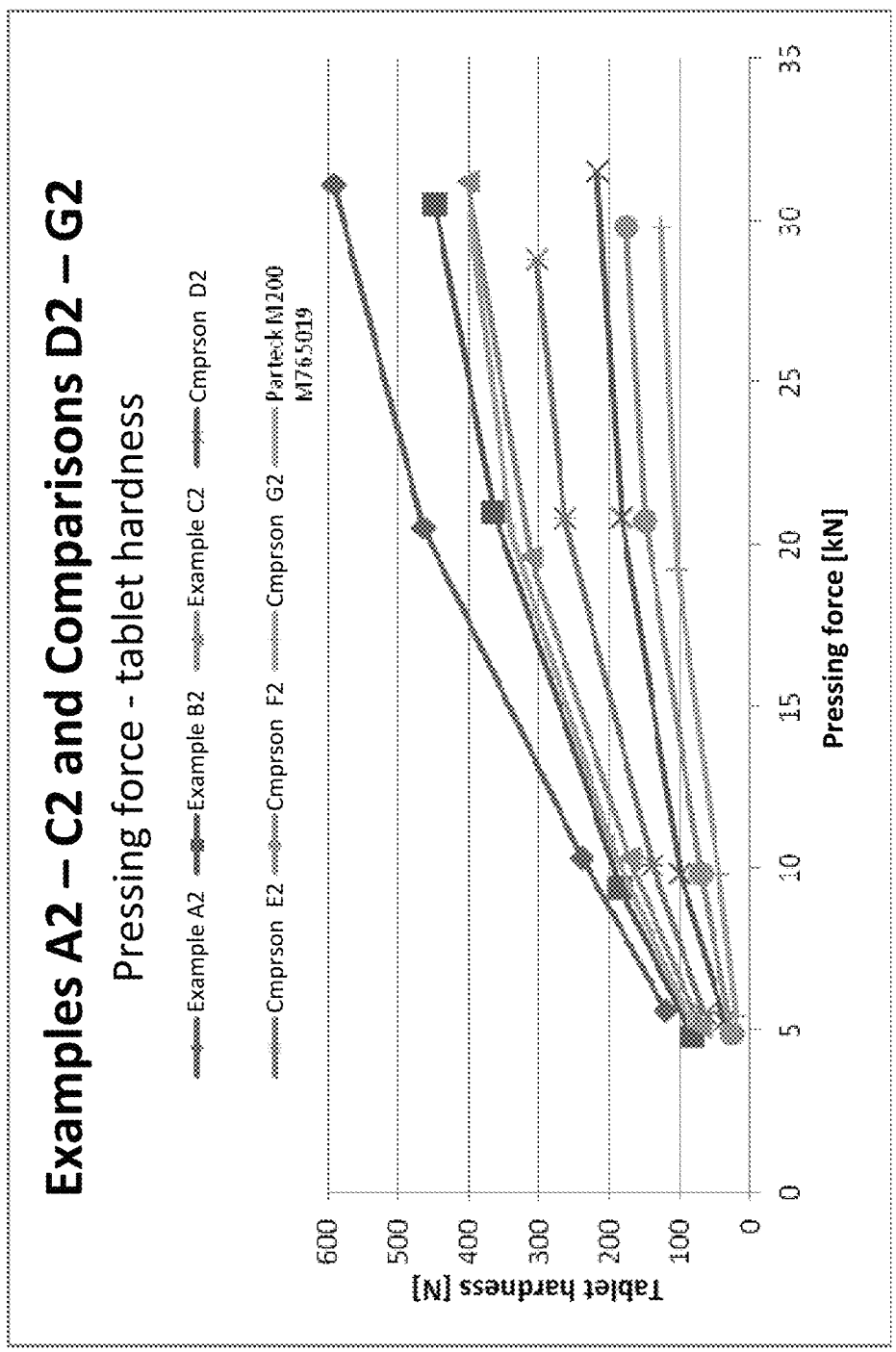

FIG. 2 shows a graph of the very different pressing force/tablet hardness profiles for better illustration.

3a. Preparation of the Blends of the Directly Compressible Excipients with the Ground PVA Grade 26-88

General description: ground PVA 26-88 is passed through an 800 μm hand sieve in order to remove any coarse components and agglomerates. 300 g of this sieved product are weighed out into a 2 l Turbula mixing vessel, 300 g of the corresponding microcrystalline cellulose from Table 3a are added and mixed for 5 min. in a T2A Turbula mixer.

TABLE 3a

Composition of the co-mixtures of ground PVA 26-88 with microcrystalline celluloses

| Composition | 50% by weight of PVA | 50% by weight of MCC |
|---|---|---|
| Example A3 | PVA 26-88* | Avicel ® PH 105 |
| Example B3 | PVA 26-88* | Vivapur ® 101 |
| Example C3 | PVA 26-88* | Avicel ® PH 101 |
| Comparison D3 | PVA 26-88* | Avicel ® PH 102 |
| Comparison E3 | PVA 26-88* | Avicel ® PH 102 SCG |
| Comparison F3 | PVA 26-88* | Vivapur ® 12 |
| Comparison G3 | PVA 26-88* | Vivapur ® 102 Premium |
| Comparison H3 | PVA 26-88* | Vivapur ® 200 |
| Comparison I3 | PVA 26-88* | Emcocel ® 90M |
| Comparison J3 | PVA 26-88* | Emcocel ® LP200 |
| Comparison K3 | PVA 26-88* | Comprecel ® M302 |

*ground PVA

3b. Compression of these Blends and Tablet Characterisation

Gen. description: 1.25 g of magnesium stearate are added to in each case 498.75 g of the co-mixtures of Examples A3-C3 or Comparisons D3-K3 prepared above in a Turbula mixing vessel, the mixture is mixed again for 5 min. in a T2A Turbula mixer and tabletted in a Korsch EK 0-DMS eccentric press.

The comparison used is Parteck® M200 blended with 1% of Parteck® LUB MST. Note: compression of Parteck® M200 with less magnesium stearate is not possible owing to the very high ejection forces which otherwise result.

TABLE 3b

Tableting data of the co-mixtures of ground PVA 26-88 with microcrystalline celluloses Key:

A: Pressing force [kN]  B: Tablet hardness after 1 day [N]
C: Tablet weight [mg]   D: Tablet height [mm]
E: Abrasion [%]         F: Ejection force (N)

| | A | | B | C | D | E | F |
|---|---|---|---|---|---|---|---|
| | Nominal | Actual | | | | | |
| Example A3 | 5 | 5.1 | 104.9 | 487.9 | 5.2 | 0.08 | 97.2 |
| | 10 | 9.0 | 190.6 | 481.6 | 4.8 | 0 | 102.7 |
| | 20 | 17.3 | 350.8 | 476.0 | 4.3 | 0 | 69.7 |
| | 30 | 27.2 | 469.7 | 473.4 | 4.1 | 0 | 43.2 |
| Example B3 | 5 | 4.9 | 93.5 | 497.9 | 5.5 | 0.33 | 98.1 |
| | 10 | 10.6 | 221.4 | 500.0 | 4.8 | 0.09 | 99.3 |
| | 20 | 20.5 | 408.6 | 503.0 | 4.4 | 0.02 | 62.8 |
| | 30 | 30.6 | 492.3 | 503.4 | 4.3 | 0.03 | 51.7 |
| Example C3 | 5 | 4.7 | 79.9 | 496.6 | 5.5 | 0.37 | 93.6 |
| | 10 | 10.5 | 201.5 | 500.1 | 4.8 | 0.05 | 93.4 |
| | 20 | 19.6 | 348.8 | 503.2 | 4.5 | 0 | 58.5 |
| | 30 | 31.3 | 424.1 | 502.9 | 4.4 | 0 | 44.8 |
| Comparison D3 | 5 | 4.9 | 70.2 | 501.8 | 5.4 | 0.49 | 85.9 |
| | 10 | 9.6 | 153.1 | 506.1 | 4.9 | 0.16 | 87.3 |
| | 20 | 18.4 | 267.3 | 506.6 | 4.5 | 0.07 | 61.1 |
| | 30 | 28.6 | 325.1 | 506.8 | 4.4 | 0.04 | 52.1 |
| Comparison E3 | 5 | 5.1 | 50.4 | 495.5 | 5.4 | 1.18 | 80.1 |
| | 10 | 9.7 | 106.3 | 499.2 | 4.8 | 0.38 | 80.9 |
| | 20 | 18.8 | 180.1 | 499.6 | 4.5 | 0.21 | 60.3 |
| | 30 | 30.2 | 209.6 | 499.7 | 4.4 | 0.16 | 55.4 |
| Comparison F3 | 5 | 4.8 | 47.6 | 496.3 | 5.6 | 1.52 | 95.3 |
| | 10 | 10.2 | 134.0 | 501.1 | 4.9 | 0.16 | 105.2 |
| | 20 | 20.7 | 251.4 | 502.9 | 4.5 | 0.06 | 75.5 |
| | 30 | 31.6 | 299.4 | 503.7 | 4.4 | 0.03 | 66.2 |
| Comparison G | 5 | 5.2 | 70.2 | 497.8 | 5.5 | 0.39 | 87.9 |
| | 10 | 9.8 | 146.5 | 498.1 | 4.9 | 0.08 | 92.4 |
| | 20 | 19.8 | 273.1 | 499.8 | 4.5 | 0.01 | 66.2 |
| | 30 | 30.8 | 331.8 | 499.9 | 4.4 | 0 | 56.8 |

TABLE 3b-continued

Tableting data of the co-mixtures of
ground PVA 26-88 with microcrystalline celluloses

| | | | | | | | |
|---|---|---|---|---|---|---|---|
| Comparison G3 | 5 | 5.1 | 76.8 | 498.4 | 5.4 | 0.26 | 91.3 |
| | 10 | 10.2 | 171.4 | 502.1 | 4.8 | 0.05 | 91.8 |
| | 20 | 19.5 | 295.7 | 503.4 | 4.5 | 0 | 66.7 |
| | 30 | 30.0 | 354.5 | 502.5 | 4.4 | 0 | 58.6 |
| Comparison H3 | 5 | 4.8 | 41.8 | 498.4 | 5.5 | 1.89 | 88.5 |
| | 10 | 9.8 | 113.0 | 502.7 | 4.9 | 0.29 | 96.4 |
| | 20 | 20.5 | 213.8 | 502.1 | 4.4 | 0.09 | 70.0 |
| | 30 | 30.4 | 244.2 | 502.6 | 4.4 | 0.07 | 64.2 |
| Comparison I3 | 5 | 4.9 | 71.0 | 494.2 | 5.5 | 0.39 | 90.9 |
| | 10 | 10.2 | 159.6 | 497.0 | 4.9 | 0.06 | 92.3 |
| | 20 | 20.0 | 273.6 | 496.8 | 4.5 | 0 | 64.8 |
| | 30 | 30.4 | 318.0 | 498.2 | 4.4 | 0 | 57.3 |
| Comparison J3 | 5 | 5.1 | 28.6 | 494.9 | 5.5 | 5.64 | 93.4 |
| | 10 | 10.0 | 78.7 | 499.2 | 4.9 | 0.46 | 97.3 |
| | 20 | 20.3 | 144.7 | 501.0 | 4.5 | 0.15 | 70.7 |
| | 30 | 29.6 | 161.2 | 501.9 | 4.4 | 0.12 | 63.9 |
| Comparison K3 | 5 | 5.1 | 39.8 | 497.6 | 5.5 | 1.50 | 90.4 |
| | 10 | 10.2 | 100.6 | 499.1 | 4.9 | 0.16 | 93.6 |
| | 20 | 19.0 | 184.2 | 500.1 | 4.5 | 0.03 | 71.6 |
| | 30 | 30.7 | 224.2 | 500.6 | 4.4 | 0.02 | 62.3 |
| Parteck ® M200 | 5 | 5.2 | 84.1 | 497.8 | 5.1 | 0.21 | 155.8 |
| | 10 | 10.7 | 196.5 | 500.6 | 4.6 | 0.17 | 306.0 |
| | 20 | 20.3 | 340.0 | 499.4 | 4.2 | 0.15 | 513.6 |
| | 30 | | 396.7 | 498.3 | 4.0 | 0.16 | 647.6 |

Figure 3:
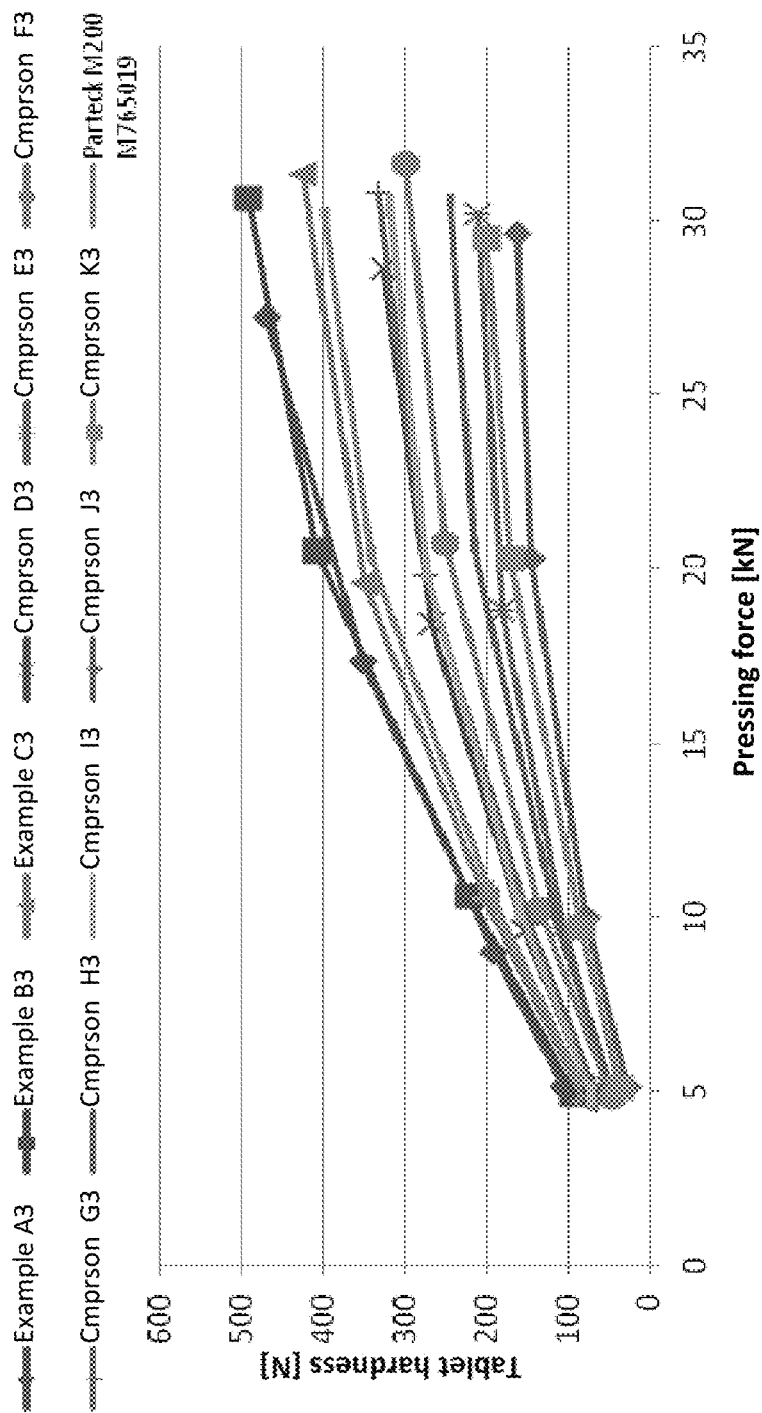

FIG. 3 shows a graph of the very different pressing force/tablet hardness profiles for better illustration.

4a. Preparation of the Blends of the Directly Compressible Excipients with the Ground PVA Grade 40-88

General description: ground PVA 40-88 is passed through an 800 μm hand sieve in order to remove any coarse components and agglomerates. 300 g of this sieved product are weighed out into a 2 l Turbula mixing vessel, 300 g of the corresponding microcrystalline cellulose from Table 4a are added and mixed for 5 min. in a T2A Turbula mixer.

TABLE 4a

Composition of the co-mixtures of ground PVA 40-88 with microcrystalline celluloses

| Composition | 50% by weight of PVA | 50% by weight of MCC |
|---|---|---|
| Example A4 | PVA 40-88* | Avicel ® PH 105 |
| Example B4 | PVA 40-88* | Vivapur ® 101 |
| Example C4 | PVA 40-88* | Avicel ® PH 101 |
| Comparison D4 | PVA 40-88* | Vivapur ® 12 |
| Comparison E4 | PVA 40-88* | Vivapur ® 102 Premium |
| Comparison F4 | PVA 40-88* | Vivapur ® 200 |
| Comparison G4 | PVA 40-88* | Emcocel ® LP200 |

*ground PVA

4b. Compression of these Blends and Tablet Characterisation

Gen. description: 1.25 g of magnesium stearate are added to in each case 498.75 g of the co-mixtures of Examples A4-C4 or Comparisons D4-G4 prepared above in a Turbula mixing vessel, the mixture is mixed again for 5 min. in a T2A Turbula mixer and tabletted in a Korsch EK 0-DMS eccentric press.

The comparison used is Parteck® M200 blended with 1% of Parteck® LUB MST. Note: compression of Parteck® M200 with less magnesium stearate is not possible owing to the very high ejection forces which otherwise result.

TABLE 4b

Tableting data of the co-mixtures of
ground PVA 40-88 with microcrystalline celluloses Key:

A: Pressing force [kN]  B: Tablet hardness after 1 day [N]
C: Tablet weight [mg]   D: Tablet height [mm]
E: Abrasion [%]         F: Ejection force (N)

| | A | | B | C | D | E | F |
|---|---|---|---|---|---|---|---|
| | Nominal | Actual | | | | | |
| Example A4 | 5 | 5.4 | 110.8 | 488.7 | 5.3 | 0.11 | 100.3 |
| | 10 | 10.4 | 235.6 | 488.4 | 4.7 | 0 | 97.4 |
| | 20 | 23.1 | 462.7 | 481.9 | 4.3 | 0 | 53.0 |
| | 30 | 29.5 | 546.4 | 485.6 | 4.2 | 0 | 44.2 |
| Example B4 | 5 | 5.1 | 88.3 | 495.9 | 5.3 | 0.41 | 82.9 |
| | 10 | 10.6 | 203.5 | 496.2 | 4.7 | 0.13 | 81.8 |
| | 20 | 19.7 | 352.1 | 501.1 | 4.4 | 0.06 | 56.7 |
| | 30 | 28.8 | 414.9 | 504.0 | 4.4 | 0.07 | 47.5 |
| Example C4 | 5 | 5.1 | 74.2 | 499.8 | 5.5 | 0.57 | 85.9 |
| | 10 | 9.6 | 152.8 | 501.6 | 5.0 | 0.19 | 87.9 |
| | 20 | 19.4 | 289.0 | 503.2 | 4.5 | 0.06 | 58.1 |
| | 30 | 29.7 | 358.2 | 503.8 | 4.4 | 0.07 | 47.5 |
| Comparison D4 | 5 | 5.0 | 35.7 | 497.3 | 5.5 | 2.89 | 81.7 |
| | 10 | 10.0 | 87.3 | 502.0 | 4.9 | 0.32 | 91.4 |
| | 20 | 20.7 | 172.5 | 502.4 | 4.5 | 0.11 | 67.6 |
| | 30 | 30.3 | 205.5 | 504.9 | 4.4 | 0.05 | 59.4 |
| Comparison E4 | 5 | 5.0 | 64.2 | 500.4 | 5.4 | 0.49 | 86.8 |
| | 10 | 10.3 | 146.9 | 505.7 | 4.9 | 0.15 | 87.3 |
| | 20 | 20.1 | 247.4 | 506.0 | 4.5 | 0.08 | 62.5 |
| | 30 | 32.0 | 296.6 | 506.0 | 4.5 | 0.07 | 55.9 |
| Comparison F4 | 5 | 5.2 | 32.9 | 497.1 | 5.5 | 3.16 | 72.9 |
| | 10 | 10.4 | 82.3 | 500.8 | 4.8 | 0.43 | 79.2 |
| | 20 | 19.6 | 149.2 | 501.2 | 4.4 | 0.18 | 60.9 |
| | 30 | 30.9 | 180.2 | 502.7 | 4.4 | 0.12 | 54.8 |
| Comparison G4 | 5 | 5.2 | 19.4 | 491.0 | 5.5 | 100.0 | 75.3 |
| | 10 | 10.0 | 45.7 | 498.5 | 5.0 | 1.26 | 80.0 |
| | 20 | 20.2 | 92.7 | 500.4 | 4.6 | 0.33 | 59.3 |
| | 30 | 31.0 | 105.9 | 501.9 | 4.5 | 0.26 | 52.6 |
| Parteck ® M200 | 5 | 5.2 | 84.1 | 497.8 | 5.1 | 0.21 | 155.8 |
| | 10 | 10.7 | 196.5 | 500.6 | 4.6 | 0.17 | 306.0 |
| | 20 | 20.3 | 340.0 | 499.4 | 4.2 | 0.15 | 513.6 |
| | 30 | 30.0 | 396.7 | 498.3 | 4.0 | 0.16 | 647.6 |

Figure 4:
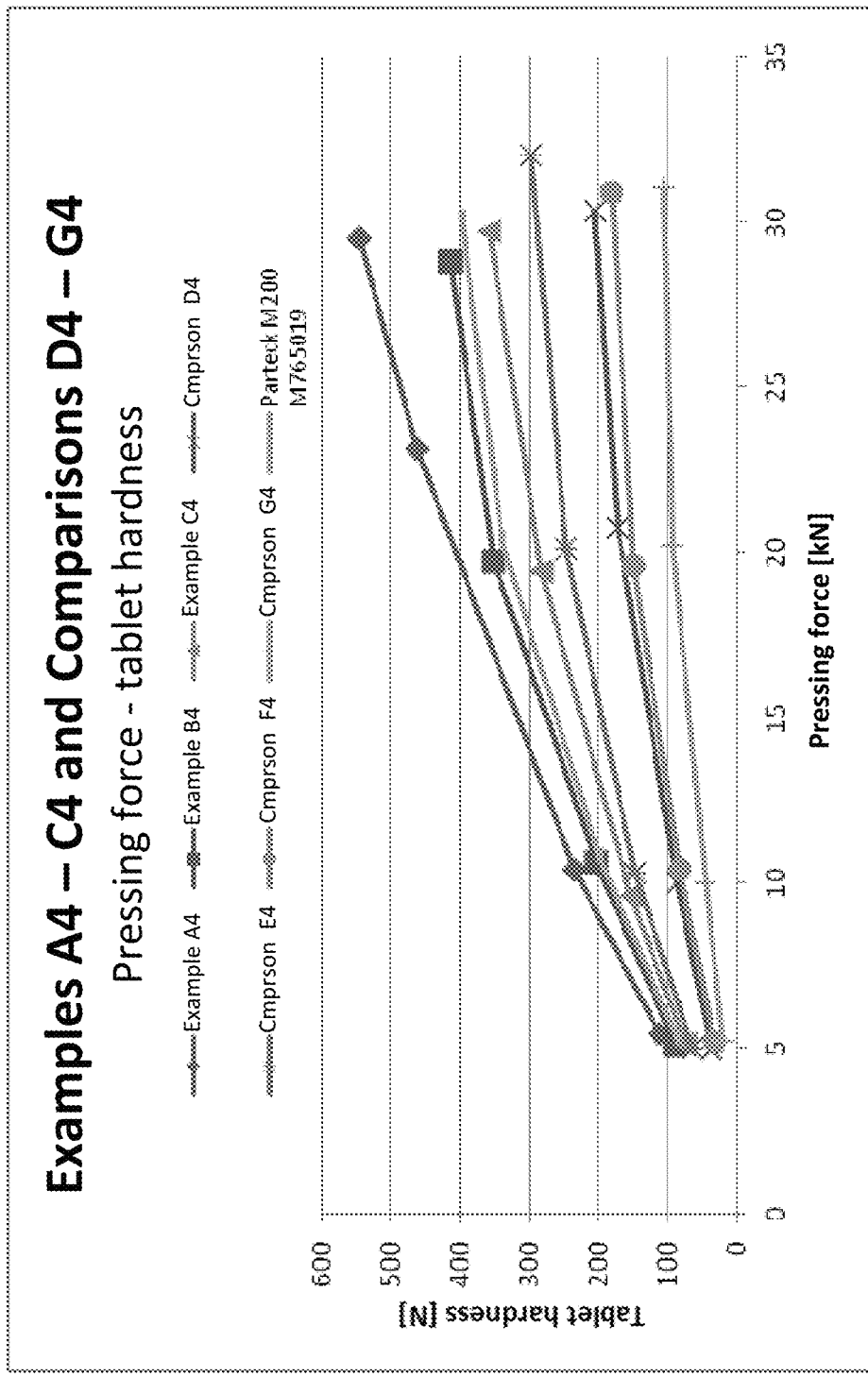

FIG. 4 shows a graph of the very different pressing force/tablet hardness profiles for better illustration.

The invention claimed is:

1. An active compound-containing tablet having extended release of active compound, comprising fine-grained polyvinyl alcohols (PVAs) and fine-grained microcrystalline celluloses (MCCs),
    wherein the polyvinyl alcohol has been ground to give a fine-grained powder having an average particle size $D_{v50}$ of 50 to 260 μm, a bulk density of 0.55 to 0.62 g/ml and an angle of repose of 35 to 38° and has been sieved through an 800 μm sieve wherein the fine-grained microcrystalline celluloses has average particle sizes of $D_{v50} < 100$ um, in any of the following measuring methods: laser diffraction with dry dispersal (1 bar counterpressure), laser diffraction with dry dispersal (2 bar counterpressure), laser diffraction with dry dispersal (3 bar counterpressure) or laser diffraction with wet dispersal (in low-viscosity silicone oil),
    and wherein the active compound has a homogeneous distribution in the tablet.

2. The active compound-containing tablet according to claim 1 having extended release of active compound of several hours, comprising a co-mixture of fine-grained polyvinyl alcohols (PVAs) and fine-grained microcrystalline celluloses (MCCs).

3. The active compound-containing tablet according to claim 1, comprising a directly compressible co-mixture comprising PVAs and MCCs in an amount in the range 1-99% by weight based on the total weight of the tablet.

4. The active compound-containing tablet according to claim 1, which, in the case of production using low pressing forces, give tablets having a hardness of up to 462 N and low friabilities of ≤0.2% by weight, but where only low ejection forces have to be used.

5. The active compound-containing tablet according to claim 1 having delayed release of active compound, comprising one or more active compounds in BCS class I, either alone or in combination with other active compounds.

6. The active compound-containing tablet according to claim 1, comprising fine-grained polyvinyl alcohols to fine-grained microcrystalline celluloses in a ratio of 5:1 to 1:5 based on weight.

7. The active compound-containing tablet according to claim 1, comprising fine-grained polyvinyl alcohols which meet the requirements of the pharmacopoeias (Ph. Eur., USP and JPE) and which are suitable for retardation of active compound.

8. The active compound-containing tablet according to claim 1, comprising fine-grained polyvinyl alcohols of grades 4-88, 18-88, 26-88 and 40-88, which meet the requirements of the pharmacopoeias Ph. Eur., JPE and USP, and grade 28-99, which meet the requirements of the pharmacopoeia pharmacopoeias JPE and Ph. Eur.

9. The active compound-containing tablet according to claim 1, comprising fine-grained polyvinyl alcohols (PVAs) which meet the requirements of the pharmacopoeia Ph. Eur. and which have been obtained by polymerisation of vinyl acetate and by subsequent partial of virtually complete hydrolysis of the polyvinyl acetate and have an average relative molecular weight in the range between 20,000 and 150,000 g/mol, and which have a viscosity, in accordance with Ph. Eur., in the range 3-70 mPa·s, (measured in a 4% solution at 20° C.) and have an ester value of not greater than 280 mg of KOH/g (degree of hydrolysis >72.2 mol %).

10. The active compound-containing tablet according to claim 1, comprising fine-grained polyvinyl alcohols (PVAs) which meet the requirements of the pharmacopoeia USP and are in the form of water-soluble, synthetic resins which are characterised by the formula $(C_2H_4O)_n$ 

in which n denotes an integer in the range of 500 to 5000, and which have been obtained by 85-89% hydrolysis of the polyvinyl acetate.

11. The active compound-containing tablet according to claim 1, comprising fine-grained polyvinyl alcohols (PVAs), which
are in the form of water-soluble, synthetic resins of the following formula $(C_2H_4O)_n$ 

in which n denotes an integer of 500 to 5000, and have been obtained by 85-89% hydrolysis of polyvinyl acetate, and have an average particle size $D_{v50}$ of 50 to 260 μm, in any of the following measuring methods: laser diffraction with dry dispersal (1 bar counterpressure), laser diffraction with dry dispersal (2 bar counterpressure), laser diffraction with dry dispersal (3 bar counterpressure) or laser diffraction with wet dispersal (in low-viscosity silicone oil), and fine-grained microcrystalline celluloses (MCCs), which
have an average particle size of $D_{v50}$<100 μm, in any of the following measuring methods: laser diffraction with dry dispersal (1 bar counterpressure), laser diffraction with dry dispersal (2 bar counterpressure), laser diffraction with dry dispersal (3 bar counterpressure) or laser diffraction with wet dispersal (in low-viscosity silicone oil).

12. The active compound-containing tablet according to claim 1, which contains at least about 50% by weight of fine-grained polyvinyl alcohols (PVAs).

13. The active compound-containing tablet according to claim 1, which is an uncoated tablet.

* * * * *